(12) United States Patent
Hattersley et al.

(10) Patent No.: US 12,329,746 B2
(45) Date of Patent: **\*Jun. 17, 2025**

(54) AR+BREAST CANCER TREATMENT METHODS

(71) Applicant: Ellipses Pharma Ltd, London (GB)

(72) Inventors: Gary Hattersley, Stow, MA (US); Jamal Saeh, Belmont, MA (US); Ziyang Yu, Wellesley, MA (US); Chris P. Miller, San Mateo, CA (US); Teeru Bihani, Boston, MA (US)

(73) Assignee: Ellipses Pharma Ltd, London (GB)

( \* ) Notice: Subject to any disclaimer, the term of this patent is extended or adjusted under 35 U.S.C. 154(b) by 0 days.

This patent is subject to a terminal disclaimer.

(21) Appl. No.: 18/478,029

(22) Filed: Sep. 29, 2023

(65) Prior Publication Data

US 2024/0207234 A1 Jun. 27, 2024

Related U.S. Application Data

(63) Continuation of application No. 16/696,110, filed on Nov. 26, 2019, now Pat. No. 11,771,682, which is a continuation of application No. 15/628,559, filed on Jun. 20, 2017, now abandoned.

(60) Provisional application No. 62/461,546, filed on Feb. 21, 2017, provisional application No. 62/377,497, filed on Aug. 19, 2016, provisional application No. 62/353,350, filed on Jun. 22, 2016.

(51) Int. Cl.
| | | |
|---|---|---|
| *A01N 43/00* | (2006.01) | |
| *A01N 43/46* | (2006.01) | |
| *A61K 31/138* | (2006.01) | |
| *A61K 31/4245* | (2006.01) | |
| *A61K 31/436* | (2006.01) | |
| *A61K 31/519* | (2006.01) | |
| *A61K 31/55* | (2006.01) | |

(52) U.S. Cl.
CPC ........ *A61K 31/4245* (2013.01); *A61K 31/138* (2013.01); *A61K 31/436* (2013.01); *A61K 31/519* (2013.01)

(58) Field of Classification Search
None
See application file for complete search history.

(56) References Cited

U.S. PATENT DOCUMENTS

| | | |
|---|---|---|
| 5,411,981 A | 5/1995 | Gaillard-Kelly et al. |
| 5,695,955 A | 12/1997 | Krstenansky et al. |
| 5,723,577 A | 3/1998 | Dong |
| 5,955,574 A | 9/1999 | Dong |
| 5,969,095 A | 10/1999 | Dong |
| 6,156,899 A | 12/2000 | Galey et al. |
| 6,159,959 A | 12/2000 | Miller |
| 6,526,316 B2 | 2/2003 | Iga et al. |
| 6,544,949 B1 | 4/2003 | Dong |
| 6,921,750 B2 | 7/2005 | Dong |
| 6,960,474 B2 | 11/2005 | Salvati et al. |
| 7,097,834 B1 | 8/2006 | Boyle |
| 7,186,683 B2 | 3/2007 | Henriksen et al. |
| 7,214,381 B2 | 5/2007 | Carrara et al. |
| 7,335,377 B2 | 2/2008 | Stern et al. |
| 7,363,075 B2 | 4/2008 | Stern et al. |
| 7,383,084 B2 | 6/2008 | Stern et al. |
| 7,410,948 B2 | 8/2008 | Dong |
| 7,446,110 B2 | 11/2008 | Kaufman et al. |
| 7,537,795 B2 | 5/2009 | Cormier et al. |
| 7,556,821 B2 | 7/2009 | Ameri et al. |
| 7,558,625 B2 | 7/2009 | Levin et al. |
| 7,579,013 B2 | 8/2009 | Ameri et al. |
| 7,612,114 B2 | 11/2009 | Hamaoka et al. |
| 7,662,404 B2 | 2/2010 | Stern et al. |
| 7,803,770 B2 | 9/2010 | Dey et al. |
| 7,960,412 B2 | 6/2011 | Hamaoka et al. |
| 7,968,580 B2 | 6/2011 | Lanter et al. |
| 8,041,421 B2 | 10/2011 | Birchall et al. |
| 8,067,448 B2 | 11/2011 | Miller |
| 8,133,505 B2 | 3/2012 | Stern et al. |
| 8,148,333 B2 | 4/2012 | Dey et al. |
| 8,268,872 B2 | 9/2012 | Miller |
| 8,455,525 B2 | 6/2013 | Miller |
| 8,629,157 B2 | 1/2014 | Berry et al. |
| 8,629,167 B2 | 1/2014 | Miller |
| 8,642,632 B2 | 2/2014 | Miller |
| 8,987,319 B2 | 3/2015 | Miller |
| 9,133,182 B2 | 9/2015 | Miller |

(Continued)

FOREIGN PATENT DOCUMENTS

| | | |
|---|---|---|
| AU | 2006201538 A1 | 5/2006 |
| EP | 0580459 A1 | 1/1994 |

(Continued)

OTHER PUBLICATIONS

Abramson, V. et al., Characterization of breast cancers with PI3K mutations in an academic practice setting using SNaPshot profiling, Breast Cancer Res Treat (2014) 145:389-399.

Lehmann, B. D. et al., PIK3CA mutations in androgen receptor-positive triple negative breast cancer confer sensitivity to the combination of PI3K and androgen receptor inhibitors, Breast Cancer Research (2014) 16:406.

(Continued)

*Primary Examiner* — Layla Soroush

(74) *Attorney, Agent, or Firm* — Choate, Hall & Stewart LLP; Kristen C. Buteau; Alisha A. Contractor

(57) ABSTRACT

A method for treating AR+ breast cancer in a subject comprising administering to the subject an AR agonist (e.g., SARMs such as RAD140), or in combination with one or more therapeutic agents selected from the group consisting of cdk4/6 inhibitors, m-TOR inhibitors, PI3k inhibitors, PARP inhibitors, BCL-2 inhibitors, and MCL-1 inhibitors.

26 Claims, 7 Drawing Sheets

(56) References Cited

U.S. PATENT DOCUMENTS

| | | |
|---|---|---|
| 9,169,254 B2 | 10/2015 | Esaki et al. |
| 9,744,149 B2 | 8/2017 | Dalton et al. |
| 9,969,683 B2 | 5/2018 | Dalton et al. |
| 10,258,596 B2 | 4/2019 | Dalton et al. |
| 11,771,682 B2 | 10/2023 | Hattersley et al. |
| 2003/0135150 A1 | 7/2003 | Kuribayashi et al. |
| 2003/0143276 A1 | 7/2003 | Hsia et al. |
| 2003/0166836 A1 | 9/2003 | Dong |
| 2004/0210080 A1 | 10/2004 | Meng et al. |
| 2005/0096586 A1 | 5/2005 | Trautman et al. |
| 2005/0106209 A1 | 5/2005 | Ameri et al. |
| 2005/0182105 A1 | 8/2005 | Nirschl et al. |
| 2005/0250749 A1 | 11/2005 | Labrie et al. |
| 2005/0261303 A1 | 11/2005 | Taniguchi et al. |
| 2005/0282749 A1 | 12/2005 | Henriksen et al. |
| 2006/0106067 A1 | 5/2006 | Shiraishi et al. |
| 2006/0116364 A1 | 6/2006 | Hamaoka et al. |
| 2006/0116415 A1 | 6/2006 | Sui et al. |
| 2006/0142387 A1 | 6/2006 | Cadilla et al. |
| 2006/0148893 A1 | 7/2006 | Blanc et al. |
| 2006/0211608 A1 | 9/2006 | Holick |
| 2006/0287327 A1 | 12/2006 | Labrie et al. |
| 2007/0088039 A1 | 4/2007 | Balog et al. |
| 2007/0155664 A1 | 7/2007 | Ranklove et al. |
| 2007/0184096 A1 | 8/2007 | Ameri et al. |
| 2007/0254875 A1 | 11/2007 | Zhi et al. |
| 2007/0281906 A1 | 12/2007 | Dalton et al. |
| 2007/0287949 A1 | 12/2007 | Levin et al. |
| 2007/0299009 A1 | 12/2007 | Dong |
| 2008/0039775 A1 | 2/2008 | Ameri et al. |
| 2008/0057068 A1 | 3/2008 | Dalton et al. |
| 2008/0114048 A1 | 5/2008 | Sui et al. |
| 2008/0119401 A1 | 5/2008 | Dong |
| 2009/0042866 A1 | 2/2009 | Lennox et al. |
| 2009/0042967 A1 | 2/2009 | Hasuoka |
| 2009/0117158 A1 | 5/2009 | Ameri et al. |
| 2009/0198189 A1 | 8/2009 | Simons et al. |
| 2009/0253758 A1 | 10/2009 | Miller |
| 2009/0264534 A1 | 10/2009 | Dalton et al. |
| 2009/0325930 A1 | 12/2009 | Hamaoka et al. |
| 2010/0004172 A1 | 1/2010 | Khan et al. |
| 2010/0041721 A1 | 2/2010 | Miller |
| 2010/0105733 A1 | 4/2010 | Lyttle et al. |
| 2010/0119568 A1 | 5/2010 | Ameri et al. |
| 2010/0152236 A1 | 6/2010 | Yamamoto et al. |
| 2010/0152649 A1 | 6/2010 | Ameri et al. |
| 2010/0160895 A1 | 6/2010 | Ameri et al. |
| 2010/0221305 A1 | 9/2010 | Armeri et al. |
| 2010/0226966 A1 | 9/2010 | Daddona |
| 2011/0092425 A1 | 4/2011 | Dey et al. |
| 2011/0172609 A1 | 7/2011 | Moga et al. |
| 2011/0224267 A1 | 9/2011 | Miller |
| 2011/0288485 A1 | 11/2011 | Tokumoto et al. |
| 2012/0004270 A1 | 1/2012 | Miller |
| 2012/0122824 A1 | 5/2012 | Birrell |
| 2013/0006217 A1 | 1/2013 | Hattersley et al. |
| 2013/0041007 A1 | 2/2013 | Miller |
| 2013/0085105 A1 | 4/2013 | Deasy et al. |
| 2013/0116288 A1 | 5/2013 | Miller |
| 2013/0157955 A1 | 6/2013 | Dey et al. |
| 2013/0217732 A1 | 8/2013 | Miller |
| 2014/0046292 A1 | 2/2014 | Hattersley et al. |
| 2014/0046293 A1 | 2/2014 | Hattersley et al. |
| 2014/0343499 A1 | 11/2014 | Zhang et al. |
| 2014/0350102 A1 | 11/2014 | Dalton et al. |
| 2016/0128968 A1 | 5/2016 | Dalton et al. |
| 2016/0146819 A1 | 5/2016 | Ince |

FOREIGN PATENT DOCUMENTS

| | | | |
|---|---|---|---|
| EP | 0916652 A1 | 5/1999 | |
| EP | 1888512 A2 | 2/2008 | |
| EP | 1911743 A1 | 4/2008 | |
| GB | 1547758 A | 6/1979 | |
| WO | WO-1994/027989 A1 | 12/1994 | |
| WO | WO-1996/035447 A1 | 11/1996 | |
| WO | WO-1996/041793 A1 | 12/1996 | |
| WO | WO-1997/002834 A1 | 1/1997 | |
| WO | WO-1997/049709 A1 | 12/1997 | |
| WO | WO-1998/030590 A2 | 7/1998 | |
| WO | WO-2001/036039 A2 | 5/2001 | |
| WO | WO-2001/049673 A2 | 7/2001 | |
| WO | WO-2002/016310 A1 | 2/2002 | |
| WO | WO-2003/011824 A1 | 2/2003 | |
| WO | WO-2003/063859 A1 | 8/2003 | |
| WO | WO-2003/068217 A1 | 8/2003 | |
| WO | WO-2003/091239 A1 | 11/2003 | |
| WO | WO-2003/096980 A2 | 11/2003 | |
| WO | WO-2003/099292 A1 | 12/2003 | |
| WO | WO-2003/105772 A2 | 12/2003 | |
| WO | WO-2004/041277 A1 | 5/2004 | |
| WO | WO-2004/041782 A1 | 5/2004 | |
| WO | WO-2004/045518 A2 | 6/2004 | |
| WO | WO-2004/080377 A2 | 9/2004 | |
| WO | WO-2004/110978 A2 | 12/2004 | |
| WO | WO-2005/000309 A2 | 1/2005 | |
| WO | WO-2005/000794 A1 | 1/2005 | |
| WO | WO-2005/000795 A2 | 1/2005 | |
| WO | WO-2005/040136 A1 | 5/2005 | |
| WO | WO-2005/042464 A1 | 5/2005 | |
| WO | WO-2005/049574 A1 | 6/2005 | |
| WO | WO-2005/049580 A1 | 6/2005 | |
| WO | WO-2005/060956 A1 | 7/2005 | |
| WO | WO-2005/073204 A1 | 8/2005 | |
| WO | WO-2005/077925 A1 | 8/2005 | |
| WO | WO-2005/085185 A1 | 9/2005 | |
| WO | WO-2005/086735 A2 | 9/2005 | |
| WO | WO-2005/087232 A1 | 9/2005 | |
| WO | WO-2005/089118 A2 | 9/2005 | |
| WO | WO-2005/090282 A1 | 9/2005 | |
| WO | WO-2005/090328 A1 | 9/2005 | |
| WO | WO-2005/094810 A2 | 10/2005 | |
| WO | WO-2005/099707 A1 | 10/2005 | |
| WO | WO-2005/102998 A1 | 11/2005 | |
| WO | WO-2005/108351 A1 | 11/2005 | |
| WO | WO-2005/110985 A2 | 11/2005 | |
| WO | WO-2005/111028 A1 | 11/2005 | |
| WO | WO-2005/115361 A2 | 12/2005 | |
| WO | WO-2005/116001 A1 | 12/2005 | |
| WO | WO-2005/120483 A2 | 12/2005 | |
| WO | WO-2006/031715 A2 | 3/2006 | |
| WO | WO-2006/039243 A1 | 4/2006 | |
| WO | WO-2006/044359 A2 | 4/2006 | |
| WO | WO-2006/044707 A1 | 4/2006 | |
| WO | WO-2006/055184 A2 | 5/2006 | |
| WO | WO-2006/060108 A1 | 6/2006 | |
| WO | WO-2006/076317 A2 | 7/2006 | |
| WO | WO-2006/113552 A2 | 10/2006 | |
| WO | WO-2006/124447 A2 | 11/2006 | |
| WO | WO-2006/133216 A2 | 12/2006 | |
| WO | WO-2007/002181 A2 | 1/2007 | |
| WO | WO-2007/005887 A2 | 1/2007 | |
| WO | WO-2007/015567 A1 | 2/2007 | |
| WO | WO-2007/034846 A1 | 3/2007 | |
| WO | WO-2007/061964 A1 | 5/2007 | |
| WO | WO-2007/067490 A1 | 6/2007 | |
| WO | WO-2007/087518 A2 | 8/2007 | |
| WO | WO-2007/099200 A1 | 9/2007 | |
| WO | WO-2007/146914 A1 | 12/2007 | |
| WO | WO-2008/002490 A2 | 1/2008 | |
| WO | WO-2008/008433 A2 | 1/2008 | |
| WO | WO-2008/011072 A2 | 1/2008 | |
| WO | WO-2008/011073 A2 | 1/2008 | |
| WO | WO-2008/024456 A2 | 2/2008 | |
| WO | WO-2008/042571 A2 | 4/2008 | |
| WO | WO-2008/044033 A1 | 4/2008 | |
| WO | WO-2008/063279 A2 | 5/2008 | |
| WO | WO-2008/063867 A2 | 5/2008 | |
| WO | WO-2008/121602 A1 | 10/2008 | |
| WO | WO-2008/124000 A2 | 10/2008 | |
| WO | WO-2008/124922 A1 | 10/2008 | |
| WO | WO-2008/127717 A1 | 10/2008 | |
| WO | WO-2008/128100 A1 | 10/2008 | |
| WO | WO-2008/130587 A2 | 10/2008 | |

(56) References Cited

FOREIGN PATENT DOCUMENTS

| WO | WO-2009/001035 A2 | 12/2008 |
|---|---|---|
| WO | WO-2009/020234 A2 | 2/2009 |
| WO | WO-2009/065600 A2 | 5/2009 |
| WO | WO-2009/081197 A1 | 7/2009 |
| WO | WO-2009/082437 A2 | 7/2009 |
| WO | WO-2009/105214 A2 | 8/2009 |
| WO | WO-2009/133861 A1 | 11/2009 |
| WO | WO-2009/137093 A1 | 11/2009 |
| WO | WO-2009/137104 A1 | 11/2009 |
| WO | WO-2009/140448 A1 | 11/2009 |
| WO | WO-2010/022176 A1 | 2/2010 |
| WO | WO-2010/118287 A1 | 10/2010 |
| WO | WO-2011/097496 A1 | 8/2011 |
| WO | WO-2011/140274 A2 | 11/2011 |
| WO | WO-2011/143469 A1 | 11/2011 |
| WO | WO-2011/150144 A2 | 12/2011 |
| WO | WO-2012/047617 A1 | 4/2012 |
| WO | WO-2012/075375 A1 | 6/2012 |
| WO | WO-2012/145665 A2 | 10/2012 |
| WO | WO-2013/082418 A1 | 6/2013 |
| WO | WO-2013/082427 A1 | 6/2013 |

OTHER PUBLICATIONS

"Deuterium." In http://www.britannica.com. Retrieved Feb. 18, 18, 2009 from <http://www.britannica.com/Ebchecked/topic/159684/deuterium>.

Acevedo, S., et al., (2008) "Selective Androgen Receptor Modulators Antagonize Apolipoprotein E4-Induced Cognitive Impairments," Letters in Drug Design & Discovery, 5:271-276.

Allan, G.F., et al., (2007) "A Selective Androgen Receptor Modulator that Reduces Prostate Tumor Size and Prevents Orchidectomy-Induced Bone Loss in Rats," J Steroid Biochemistry & Molecular Biology, 103:76-83.

Allan, G.F., et al., (2007) "A Selective Androgen Receptor Modulator with Minimal Prostate Hypertrophic Activity Enhances Lean Body Mass in Male Rats and Stimulates Sexual Behavior in Female Rats," Endocr, 32:41-51.

Ameri, M., et al., "Demonstrated Solid-State Stability of Parathyroid Hormone PTH(1-34) Coated on a Novel Transdermal Microprojection Delivery System," Pharmaceutical Res, 26(11):2454-2463 (published online Sep. 3, 2009).

Ameri, M., et al., (2010) "Parathyroid Hormone PTH(1-34) Formulation that Enables Uniform Coating on a Novel Transdermal Microprojection Delivery System," Pharmaceutical Res, 27(2):303-313 (published online Dec. 15, 2009).

Anderson, A C., (2003) The Process of Structure-Based Drug Design, Chem. Biol. 10:787-797.

Arun, B., et al., (2002) "The Search for the Ideal SERM," Expert Opinion Pharmacotherapy, 3(6):681-691.

Autoimmune disorders: MedlinePlus Medical Encyclopedia [online], [retrieved on Jun. 3, 2011]. Retrieved from the Internet URL: http://www.nlm.nih.gov/medlineplus/ency/article/000816.htm.

Bell, Sarah L., et al., Genetic Engineering of Hybridoma Glutamine Metabolism, Enzyme and Microbial Technology 17; 98-106, 1995, Elsevier Science Inc.

Bogani, C., et al., (2013) "mTOR Inhibitors Alone and in Combination with JAK2 Inhibitors Effectively Inhibit Cells of Myeloproliferative Neoplasms," PLoS One 8(1 ): e54826.

Bohl, C.E., (2005) "Structural Basis for Antagonism and Resistance of Bicalutamide in Prostate Cancer," PNAS, 102(17):6201-6206.

Bohl, C.E., et al., (2005) "Structural Basis for Accommodation of Nonsteroidal Ligands in the Androgen Receptors," J Biol Chem, 280(45):37747-37754.

Browne, (1997) "Stable Isotopes in Pharamaceutical Research," Pharmacochem istry Library, 26: 13-18.

Cantin, L., et al., (2007) "Structural Characterization of the Human Androgen Receptor Ligand-Binding Domain Complexed with EM57 44, a Rationally Designed Steroidal Ligand Bearing a Bulky Chain Directed Toward Helix 12," J Biological Chem, 282(42):30910-30919.

Carlson, Kathryn E., et al.,Altered Ligand Binding Properties and Enhanced Stability of a Constitutively Active Estrogen Receptor: Evidence That An Open Pocket Conformation Is required For Ligan Interaction, Biochemistry, 1997, 36, 14897-14905, American Chemical Society.

Cesnjaj, et al., (1991) "In Vivo Models in the Study of Osteopenias," Eur J Clinical Chem and Clinical Biochem, 29(4):211-219.

Chou, Ting-Chao, et al., Quantitative Analysis of Dose-Effect Relationships: The Combined Effects of Multiple Drugs or Enzyme Inhibitors, Adv. Enzyme Regul., 27-55, 1984.

Clinical Trials.gov, "A Study for the Transdermal Application of Teriparatide," Retrieved from: http://www.clinicaltrials.gov/ct2/show/NCT01011556?term=pth+patch&rank= 8, Date Retrieved: Sep. 18, 2012, 6 pages.

Clinical Trials.gov, "Dose Ranging Study—Macroflux PTH in Postmenopausal Women With Osteoporosis," Retrieved from: http://www.clinicaltrials.gov/ct2/show/NCT00489918?term=pth+patch&rank=1, Date Retrieved: Sep. 18, 2012, 1 page.

CN 201280030749X Chinese Patent Office, Chinese Patent Search Report for 2012800307 49X dated Feb. 16, 2015.

Cosman, F., et al., (2009) "Effect of Transdermal Teriparatide Administration on Bone Mineral Density in Postmenopausal Women," J Clin Endocrinol Metab, 95(1): 151-158 (published on line Oct. 26, 2009).

Coss, C.C. et al., Selective androgen receptor modulators as improved androgen therapy for advanced breast cancer, Steroids, 90:94-100 (2014).

Coss, Christopher C., et al. Selective Androgen Receptor Modulators as Improved Androgen Therapy for advance Breast Cancer; Steroids, Elsevier Science publishers, Jun. 16, 2014, Vo. 90, pp. 94-100.

Daddona, Peter E., et al., (2011) "Parathyroid Hormone (1-34)-Coated Microneedle Patch System: Clinical Pharmacokinetics and Pharmacodynamics for Treatment of Osteoporosis," Pharm Res, 28: 159-165 (published on line Jun. 22, 2010).

Dalton, J. T., et al., (2011) "The Selective Androgen Receptor Modulator GTx-024 (Enobosarm) Improves Lean Body Mass and Physical Function in Healthy Elderly Men and Postmenopausal Women: Results of a Double-Blind, Placebo-Controlled Phase II Trial," J. Cachexia Sarcopenia Muscle 2:153-161.

Davey, R.A. and Grossman, M., Androgen Receptor Structure, Function and Biology: From Bench to Bedside, Clin. Biochem. Rev., 37(1):3-15 (2016).

Dawson, S.J., et al., BCL2 in Breast Cancer: A Favourable Prognostic Marker Across Molecular Subtypes and Independent of Adjuvant Therapy received, Bristish Journal of Cancer (2010) 103, 668-675.

Dean, T., et al., (2008) "Altered Selectivity of Parathyroid Hormone (PTH) and PTH-Related Protein (PTHrP) for Distinct Conformations of the PTH/PTHrP Receptor", Molecular Endocrinology, 22(1 ): 156-166.

Deschamps, P., et al., (2005) "The Saga of Copper(II)-L-histidine," Coordination Chem Reviews, 249:895-909.

Dienstmann, R., et al., (2014) "Picking the Point of Inhibition: A Comparative Review of PI3K/AKT/mTOR Pathway Inhibitors," Mal. Cancer Ther. 13(5): 1021-1031.

Ferrandon, S., et al., "Sustained cyclic AMP production by parathyroid hormone receptor endocytosis", Nature Chemical Biology, 5(10):734-7 42 (Oct. 2009).

Fribbens et al. (Plasma ESR1 Mutations and the Treatment of Estrogen Receptor-Positive Advanced Breast Cancer. J. Clin. One. vol. 34, No. 25, Sep. 1, 2016, epub Jun. 6, 2016.) (Year: 2016).

Gao, W., et al., (2004) "Comparison of the Pharmacological Effects of a Novel Selective Androgen Receptor Modulator, the 5a-Reductase Inhibitor Finasteride, and the Antiandrogen Hydroxyflutamide in Intact Rats: New Approach for Benign Prostate Hyperplasia," Endocrinology, 145(12):5420-5428.

Gao, W., et al., (2005) "Selective Androgen Receptor Modulator (SARM) Treatment Improves Muscle Strength," Endocrinology, doi: 10.121 0/en.2005-0572, pp. 1-37.

(56) References Cited

OTHER PUBLICATIONS

Gao, W., et al., (2005) "Selective Androgen Receptor Modulator Treatment Improves Muscle Strength and Body Composition and Prevents Bone Loss in Orchidectom ized Rats," Endocrinology, 146(11):4887-4897.

Gao, W., et al., (2007) "Expanding the Therapeutic use of Androgens via Selective Androgen Receptor Modulators (SARMs)," Drug Discovery Today, 12:241-248.

Gao, W., et al., (2007) "Ockham's Razor and Selective Androgen Receptor Modulators (SARMs): Are we Overlooking the Role of 5a-Reductase?", Molecular Interventions, 7: 10-13.

Garland, M.J., et al., (2011) "Microneedle arrays as medical devices for enhanced transdermal drug delivery," Expert Rev Med Devices, 8(4):459-482.

Gill, H.S. and Prausnitz, M.R., (2007) "Coating Formulations for Microneedles," Pharmaceutical Res, 24(7): 1369-1380.

Gitto, S. B., et al., (2015) "Recent Insights into the Pathophysiology of mTOR Pathway Dysregulation," Res. Rep. Biol. 2:1-16.

Hamann, L.G., "Discovery and Preclinical Profile of a Highly Potent and Muscle Selective Androgen Receptor Modulator (SARM)," 227th National Meeting of the American Chemical Society Medicinal Chemistry Division, Mar. 28, 2004, Anaheim, CA.

Hamann, L.G., et al., (2007) "Tandem Optimization of Target Activity and Elimination of Mutagenic Potential in a Potent Series of N-aryl Bicyclic Hydantoin-Based Selective Androgen Receptor Modulators," Bioorganic & Medicinal Chem Letters, 17: 1860-1864.

Hanada, K., et al., (2003) "Bone Anabolic Effects of S-40503, a Novel Nonsteroidal Selective Androgen Receptor Modulator (SARM), in Rat Models of Osteoporosis," Biol Pharm Bull, 26(11 ): 1563-1569.

Hickey, T.E. et al., Minireview: The androgen receptor in breast tissues: growth inhibitor, tumor suppressor, oncogene? Mol. Endocrinol., 26(8):1252-1267 (2012).

Higuchi, R.I., et al., (2007) "Novel Series of Potent, Nonsteroidal, Selective Androgen Receptor Modulators Based on 7 H-[1,4]Oxazino[3,2-g]quinolin-7- ones," J Medicinal Chem, pp. A-K (Apr. 17, 2007).

Higuchi, R.I., et al., (2007) "Novel Series of Potent, Nonsteroidal, Selective Androgen Receptor Modulators Based on 7 H-[1,4]Oxazino[3,2-g]quinolin-7-ones," J Med Chem, 50(10):2486-2496.

Holford, Nicholas H.G., et al., Understanding the Dose-Effect Relationship: Clinical Applicatio of Pharmacokinetic-Pharmacodynamic Models, Clinical Pharmacokinetics 6: 429-453 (1981), ADIS Press Australasia Pty. Ltd.

Horig, H. and Pullman, W., (2004) "From Bench to Clinic and Back: Perspective on the 1st IQPC Translational Research Conference," J Translational Medicine, 2(44):1-8.

Hosford, Sarah, et al., Clinical Potential of Novel Therapeutic Targets in Breast Cancer: CDK4/6, Src, JAK/STAT, PARP, HDAC, and PI3K/AKT/mTOR Pathways, Pharmacogenomics and Personalized Medicine, 2014:7 pp. 203-215, Dove Press.

Huang, Wei, et al., A Newfound Cancer-Activating Mutation reshapes the Energy Landscape of Estrogen-Binding Domain, Journal of Chemical Theory and Computation, 2014, 10, 2897-2900, American Chemical Society.

Hwang, D.J., et al., (2006) Arylisothiocyanato Selective Androgen Receptor.

Jayaraman, A. et al., Selective androgen receptor modulator RAD140 is neuroprotective in cultured neurons and kainate-lesioned male rats, Endocrinology, 155(4):1398-1406 (2014).

Kalluri, H. and Banga, A. K., "Transdermal Delivery of Proteins," AAPS PharmSciTech, 12(1) 431-441 (published online Mar. 3, 2011).

Kamberi, M., (2005) The effects of sucrose on stability of human brain natriuretic peptide [hBNP(1-32)] and human parathyroid hormone (hPTH(1-34)], J Peptide Res, 66:348-356.

Kaplan, B., et al., (2014) "Strategies for the Management of Adverse Events Associated with mTOR Inhibitors," Transplant. Rev. 28(3): 126-133.

Katikaneni, S., et al., (2010) "Transdermal delivery of ~13 kDa protein-an in vivo comparison of physical enhancement methods", J Drug Targeting, 18(2):141-147.

Keaveny, Tony M., et al., Femoral Strength in Osteoporotic Women Treated with teriparatide or Alendronate, Bone 50 (2012) 165-170, Elsevier.

Kemppainen, J.A., et al., (1999) "Distinguishing Androgen Receptor Agonists and Antagonists: Distinct Mechanisms of Activation by Medroxyprogesterone Acetate and Dihydrotestosterone," Molecular Endocrinology, 13:440-454.

Kenan, Y., et al., "Comparison of Transdermal and Subcutaneous Teriparatide Pharmacokinetics and Pharmacodynamics of Bone Markers in Postmenopausal Women," Poster Session, Presentation No. FR0376 of the ASBMR 2010 Annual Meeting, (Oct. 15-16, 2010).

Kilbourne, E.J., et al., (2007) "Selective Androgen Receptor Modulators for Frailty and Osteoporosis," Current Opinion in Investigational Drugs, 8(10):821-829.

Kim, J., et al., "The 4-Para Substituent of S-3-(phenoxy)-2-hydroxy-2-methyl-N-(4-nitro-3-trifluoromethyl-phenyl)-propionamides is a Major Structural Determinant of In Vivo Disposition and Activity of Selective Androgen Receptor Modulators," JPET #88344, DOI: 10.1124/jpet.105.088344, 42 pages (Jun. 29, 2005).

Kinoyama, I., et al., (2006) "(+)-(2R,5S)-4-[4-Cyano-3-(trifluoromethyl)phenyl]- 2, 5-d imethyl-N-[6-(trifluoromethyl)pyrid in-3-yl] piperazine-1-carboxam ide (YM580) as an Orally Potent and Peripherally Selective Nonsteroidal Androgen Receptor Antagonist," J Med Chem, 49(2): 716-726.

Lamb, R., et al., (2013) "Cell Cycle Regulators Cyclin D1 and CDk4/6 Have Estrogen Receptor-Dependent Divergent Functions in Breast Cancer Migration and Stem Cell-Like Activity," Cell Cycle 12( 15):2384-2394.

Lanter, J.C., et al., (2007) "The Discovery of a Potent Orally Efficacious Indole Androgen Receptor Antagonist Through in vivo Screening," Bioorganic & Medicinal Chem Letters, 17:123-126.

Leder, Benjamin Z., et al., Two Years of Denosumab and Teriparatide Administration in Postmenopausal Women With osteoporosis (The Data Extension Study): A Randomized Controlled Trial, NIH Public Access, Lancet Jul. 6, 2013, 382(9886); 50-56, The Endocrine Society.

Li et al. (Endocrine-Therapy-Resistant ESR1Variants Revealed by Genomic Characterization of Breast-Cancer-Derived Xenografts Cell Reports4, 1116-1130, Sep. 26, 2013). (Year: 2013).

Li, Shunqiang, et al., Endocrine-therapy-Resistant ESR1 Variants Revealed by Genomic Characterization of Breast-Cancer-Derived Xenografts, Cell Reports 4, 1116-1130, Sep. 26, 2013; The Authors.

Lindeman, Geoffrey J., et al., Abstract IA19: Targeting the BCL-2 Family in Breast Cancer, Molecular Cancer Research, AACR Special Conference:Advances in Breast Cancer; Oct. 17-20, 2015.

Lloyd, M.E., et al., (1996) "Relation Between Insulin-Like Growth Factor-I Concentrations, Osteoarthritis, Bone Density, and Fractures in the General Population: the Chingford Study," Ann Rheum Dis, 55:870-874.

Loewe. S. et al., Uber Kombinationswirkungen, Aus dem Pharmakologischen Institut der Universitat Tartu-Dorpat, Archiv fur Exp Path and Pharm, 1926, 313-326.

Loprinzi, C.L., et al., (2001) "Management of Hot Flashes in Breast-Cancer Survivors," Lancet Oncology, 2(4): 199-204.

Love, Richard R., M.D., et al., Effects of Tamoxifen on Bone Mineral Density in Postmenopausal Women with Breast Cancer, The New England Journal of Medicine, vol. 326, No. 13, pp. 852-856, Mar. 26, 1992, Massachusetts Medical Society.

Ma, Y.L., et al., (2005) "Raloxifene and Teriparatide (hPTH 1-34) Have Complementary Effects on the Osteopenic Skeleton of Ovariectomized Rats," J Bone Mineral Metab, 23 (Supp.) 62-68 (2005).

Martinborough, E., et al., (2007) "Substituted 6-(1-pyrrolidine)-quinolin- 2(1 H)-ones as Novel Selective Androgen Receptor Modulators." J Med Chem, 50:5049-52.

(56) References Cited

OTHER PUBLICATIONS

McGinley, P.L., et al., (2007) "Circumventing Anti-Androgen Resistance by Molecular Design," J Am Chem Soc, 129:3822-3823.
Medi, B.M. and Singh, J., (2003) "Electronically Facilitated Transdermal Delivery of Human Parathyroid Hormone (1-34)," International J Pharmaceutics, 263:25-33.
Mesu, J. G., et al., (2005) "Infrared and Raman Spectroscopic Study of pHinduced Structural Changes of L-histidine in Aqueous Environment," Vibrational Spectroscopy, 39: 114-125.
Miao, D., et al., (2005) "Osteoblast-derived PTHrP is a Potent Endogenous Bone Anabolic Agent that Modifies the Therapeutic Efficacy of Administered PTH 1-34," J Clin Invest, 115(9):2402-2411.
Miller, C.P. et al., Design, Synthesis, and Preclinical Characterization of the Selective Androgen Receptor Modulator (SARM) RAD140, ACS Med. Chem. Lett., 2(2):124-129 (2010).
Miller, C.P., et al., (2010) "Design, Synthesis, and Preclinical Characterization of the Selective Androgen Receptor Modulator (SARM) RAD140," ACS Med Chem Lett, 2(2):124-129, DOI: 10.1021/ml1002508 (Dec. 2, 2010).
Miller, C.P., et al., (2010) "Synthesis of Potent, Substituted Carbazoles as Selective Androgen Receptor Modulators (SARMs)," Bioorg Med Chem Lett, 20:7516-7520.
Mitchell, Clint, et al., Inhibition of MCL-1 in Breast Cancer Cells Promotes Cell Death in Vitro and in Vivo, Cancer Biology & Therapy, vol. 10, Issue 9, pp. 903-917, Nov. 1, 2010, Landes Bioscience.
Mitchell, H.J., et al., (2009) Design, Synthesis, and Biological Evaluation of 16-Substituted 4-Azasteroids as Tissue-Selective Androgen Receptor Modulators (SARMs), J Med Chem, 52(15):4578-81.
Modulators (SARMs) for Prostate Cancer, Bioorganic & Medicinal Chem, 14:6525-6538.
Mohler, M.L., et al., (2009) "Nonsteroidal Selective Androgen Receptor Modulators (SARMs): Dissociating the Anabolic and Androgenic Activities of the Androgen Receptor for Therapeutic Benefit," J Med Chem, 52(12):3597-617.
Morris, J.J., et al., (1991) "Non-steroidal Antiandrogens. Design of Novel Compounds Based on an Infrared Study of the Dominant Conformation and Hydrogen-Bonding Properties of a Series of Anilide Antiandrogens," J Med Chem, 34:447-455.
Nahta, Rita, et al., Bcl-2 Antisense Oligonucleotides: A Potential Novel Strategy for the Treatment of Breast Cancer, Seminars in Oncology, vol. 30, No. 5, Suppl 16, Oct. 2003, pp. 143-149.
Narayanan, et al., (2014) "Selective Androgen Receptor Modulators (SARMs) Negatively Regulate Triple-Negative Breast Cancer Growth and Epithelial:Mesenchymal Stem Cell Signaling," PLoS One, vol. 9, Iss. 7, e103202.
Narayanan, R., et al., (2008) "Selective Androgen Receptor Modulators in Preclinical and Clinical Development," Nuclear Receptor Signaling, 6:e010.
Ng, R.A., (2007) "Synthesis and SAR of Potent and Selective Androgen Receptor Antagonists: 5,6-Dicholoro-benzimidazole Derivatives," Bioorganic & Medicinal Chemistry Letters, 17:784-788.
Ng, R.A., (2007) "Synthesis of Potent and Tissue-Selective Androgen Receptor Modulators (SARMs): 2-(2,2,2)-Trifluoroethyl-benzimidazole Scaffold," Bioorganic & Medicinal Chemistry Letters, 17: 1784-1787.
Obinata, R., et al., (2010) "Stereodivergent Construction of Aminidiols with a CF3 Group," Organic Letters, 12(19):4316-9.
Oesterreich, Steffi, et al., The Search for ESR1 Mutations in Breast Cancer; Nature Genetics, vol. 45, No. 12 pp. 1415-1416, Dec. 2013, Nature American Inc.
Okazaki, M., et al., (2008) "Prolonged signaling at the parathyroid hormone receptor by peptide ligands targeted to a specific receptor conformation," PNAS, 105(43): 16525-16530.
O'Leary, B., et al., (2016) "Treating Cancer with Selective CDK4/6 Inhibitors," Nat. Rev. Clin. Oneal. 13:417-430.
Ornoy, et al., (1995) "Osteoporosis: Animal Models for the Human Disease," Animal Models of Human Related Calcium Metabolic Disorders, 105-126.
Ostrowski, J., et al., (2007) "Pharmacological and X-Ray Structural Characterization of a Novel Selective Androgen Receptor Modulator: Potent Hyperanabolic Stimulation of Skeletal Muscle with Hypostimulation of Prostate in Rats," Endocrinology, 148(1):4-12.
Overmoyer, B., et al., Abstract OT2-01-06: Phase 2 open label, multinational, randomized, parallel design study investigating the efficacy and safety of GTx-024 on metastatic (MET) or locally advanced (LA) ER+/AR+ breast cancer (BC) in postmenopausal (PM) women, pp. 1-2; 38th Ann CTRC-AACR San Antonio Breast Cancer Symposium, Dec. 8-12, 2015; Published Feb. 2016, Ongoing Clinical Trials.
Pallet, N., et al., (2012) "Adverse Events Associated with mTOR Inhibitors," Exp. Opin. Drug Saf. 12(2): 177-186.
Pandya, K.J., et al., (2004) "Pilot Study Using Gabapentin for Tamoxifen-Induced Hot Flashes in Woment with Breast Cancer," Breast Cancer Res Treatment, 83:87-89.
Paudel, K.S., et al., (2010) "Challenges and opportunities in dermal/transdermal delivery," Ther Del iv, 1 (1):109-131.
PCT/EP1996/01962 European Patent Office, International Search Report for PCT/EP1996/01962 completed Sep. 3, 1996 and mailed Sep. 16, 1996.
PCT/US17/26462 United States Patent and Trademark Office, International Search Report and Written Opinion for PCT/US17/26462 completed Jun. 6, 2017 and mailed Jul. 3, 2017.
PCT/US17/38390 International Search Report dated Aug. 18, 2017.
PCT/US1997/22498 European Patent Office, International Search Report for PCT/US1997/22498 completed Nov. 13, 1998 and mailed Dec. 23, 1998.
PCT/US2006/044921 Korean Intellectual Property Office, International Search Report for PCT/US2006/044921 completed Mar. 14, 2007 and mailed Mar. 15, 2007.
PCT/US2007/014598 European Patent Office, International Search Report and Written Opinion completed Mar. 7, 2008 and mailed Mar. 28, 2008 for PCT/US2007/014598.
PCT/US2009/001035 European Patent Office, International Search Report and Written Opinion completed Jul. 29, 2009 and mailed Aug. 7, 2009 for PCT/US2009/001035.
PCT/US2009/002868 European Patent Office, International Search Report and Written Opinion completed Jul. 27, 2009 and mailed Aug. 3, 2009 for PCT/US2009/002868.
PCT/US2009/002885 European Patent Office, International Search Report and Written Opinion completed Aug. 14, 2009 and mailed Sep. 10, 2010 for PCT/US2009/002885.
PCT/US2009/054348 United States Patent and Trademark Office, International Search Report and Written Opinion for PCT/US2009/054348 completed Dec. 3, 2009 and mailed Dec. 9, 2009.
PCT/US2010/030480 United States Patent and Trademark Office, International Search Report and Written Opinion completed Jun. 1, 2010 and mailed Jun. 9, 2010 for PCT/US2010/030480 issued Oct. 11, 2011.
PCT/US2011/023768 European Patent Office, Extended Search Report and Written Opinion for PCT/US2011/023768 (EP11740437, WO2011097496) completed Apr. 22, 2013 and mailed Apr. 26, 2013.
PCT/US2011/023768 United States Patent and Trademark Office, International Search Report and Written Opinion completed Mar. 15, 2011 and mailed Mar. 25, 2011 for PCT/US2011/023768 issued Aug. 7, 2012.
PCT/US2011/036311 United States Patent and Trademark Office, International Search Report and Written Opinion completed Aug. 2, 2011 and mailed Aug. 12, 2011 for PCT/US2011/036311 issued Nov. 13, 2012.
PCT/US2011/053375 European Patent Office, International Search Report and Written Opinion completed Dec. 19, 2011 and mailed Jan. 16, 2012 for PCT/US2011/053375.
PCT/US2011/063034 Australian Patent Office, International Search Report for PCT/US2011 /063034 completed Mar. 15, 2012 and mailed Mar. 19, 2012.
PCT/US2012/034510 United States Patent and Trademark Office, International Preliminary Report on Patentability (Ch I) for PCT/US2012/034510 issued Mar. 18, 2014.

(56) References Cited

OTHER PUBLICATIONS

PCT/US2012/34510 United States Patent and Trademark Office, International Search Report and Written Opinion for PCT/US2012/34510 completed Aug. 11, 2012 and mailed Aug. 31, 2012.
Perumal, 0., et al., (2013) "Turning Theory into Practice: The Development of Modern Transdermal Drug Delivery systems and Future Trends," Skin Pharmacol Physiol, 26:331-342.
Piu, F., et al., (2008) "Pharmacological Characterization of AC-262536, A Novel Selective Androgen Receptor Modulator," J Steroid Biochemistry & Molecular Biology, 109:129-137.
Riedmaier, I., et al., (2009) "Influence of testosterone and a Novel SARM on Gene Expression in Whole Blood of Macaca fascicularis," J Steroid Biochemistry and Molecular Biology, 114: 167-173.
Rochira, V., et al., (2006) "Osteoporosis and Male Age-Related Hypogonadism: Role of Sex Steroids on Bone (patho)Physiology," Eur J Endocrinol, 154: 175-185.
Rogol, AD., "Causes of Short Stature," UptoDate, pp. 1-15, accessed May 2, 2016 at http://www.uptodate.com/contents/causes-of-shortstature?topicKey=PEDS%2F5832&elaps . . . .
Rosen, Clifford J., MD, Postmenopausal Osteoporosis, The New England Journal of Medicine, Clinical Practice, Aug. 11, 2005; 353:6;595-603, Massachusetts Medical Society.
Rosenblatt, M., (2009) "When Two Keys Fit One Lock, Surprises Follow",Nature Chem. Biol. 5(10):707-708.
Salvati, M.E., et al., (2008) "Identification and Optimization of a Novel Series of [2.2.1 ]-oxabicyclo imide-based Androgen Receptor Antagonists," Bioorganic & Medicinal Chem Letters, 18: 1910-1915.
Schafer, S. and Kokhof, P., (2008) "Failure is an Option: Learning From Unsuccessful Proof-of-Concept Trials," Drug Discovery Today, 13(21 /22):913-916.
Schiavon, Gaia, et al., Analysis of ESR1 Mutations in Circulating Tumor DNA Demonstrates Evolution During Therapy for Metastatic Breast Cancer, Research Article, Cancer, www.sciencetranslationmedicine.org; Nov. 11, 2015, vol. 7, Issue 313 313ra182, pp. 1-8.
Shao, Jieya, et al., ESR1 Gene Fusions Implicated in Endocrine Therapy Resistance of ER+ Breast Cancer; Cancer Research, May 1, 2015, vol. 75, No. 9, Suppl. Abstact No. PD6-4; 37th Ann CTRC-AACR San Antonio Breast Cancer Symposium, Am Assoc. for Cancer Research, Inc.; hhtps://stnwebjapan.cas.org/cgi-gin/sdcgi?S ID= 101373-1363788773-300&APP=stnwebt&.
Smith, Susan Y. et al., Eldecalcitol, a Vitamin D Analog, Reduces Bone turnover and Increases Trabecular and Cortical Bone Mass, Density, and Strength in Ovariectomized Cynomolgus Monkeys, Bone 57 (2013) 116-122, Elsevier Inc.
Solomon, Zachary J., et al., Selective Androgen Receptor Modulators (SARMs) Current Knowledge and Clinical Applications, Sex Med Rev., Jan. 2019, 7(1): 84-94 doi: 10.1016/j.sxmr.2018.09.006.
Stellman, J.T., (2009) "Development, Production and Characterization of Plastic Hypodermic Needles," MS Thesis, Georgia Institute of Technology, pp. 1-150.
Sterns, V., et al., (2000) "A Polot Trial Assessing the Efficicy of Paroxetine Hydrochloride (Paxil ©) in Controlling Hot Flashes in Breast Cancer Survivors," Annals of Oncology, 11: 17-22.
Sun, C., et al., (2006) "Discovery of Potent, Orally-Active, and Muscle-Selective Androgen Receptor Modulators Based on an N-Arylhydroxybicyclohydantoin Scaffold," J Med Chem, 49(26):7596-7599.
Sundar, et al., (2012) "Spironolactone, a possible selective androgen receptor modulator, should be used with caution in patients with metastatic carcinoma of the prostate," BMJ Case Rep, (Feb. 25, 2012), Abstract.
Supplementary Partial European Search Report for EP17816081.8, 10 pages, (2020).
Suzuki, Y., et al., (2001) "Iontophoretic Pulsatile Transdermal Delivery of Human Parathyroid Hormone (1-34)," J Pharmacy and Pharmacology, 53(9): 1227-1234.
Takeshita, Takashi, et al., Clinical Significance of Monitoring ESR1 Mutations in Circulating Cell-Free DNa in Estrogen Receptor Positive Breast Cancer Patients, Oncotarget, vol. 7, No. 22, Apr. 19, 2016; www.impactjournals.com/oncotarget.
Thiel, K.A., (2004) "Structure-aided drug design's next generation," Nature Biotechnol, 22(5):513-519.
Toy et al (ESR 1 ligand-binding domain mutations in hormoneresistant breast cancer. Nature Genetics vol. 45 1 No. 12 1 Dec. 2013) (Year: 2013).
Tucker, H., et al., (1988) "Nonsterodial Antiandrogens, Synthesis and Structure-Activity Relationships of 3-Substituted Derivatives of 2-Hydroxypropionanilides," J Med Chem,31 :954-959.
Vajda, E.G., et al., (2009) "Pharmacokinetics and Pharmacodynamics of LGD-3303 [9-Cholor-2-ethyl-1-methyl-3-(2,2,2-trifluoroethyl)-3H-pyrrolo-[3,2-f]quinolin-7(6H)-one], an Orally Available Nonsteroidal-Selective Androgen Receptor Modulator," J Pharmacology and Experimental Therapeutics, 328(2):663-670.
Van der Maaden, K., et al., (2012) "Microneedle technologies for (trans)dermal drug and vaccine delivery", J Controlled Release, 161:645-655.
Van Oeveren, A, et al., (2007) "Novel Selective Androgen Receptor Modulators: SAR Studies on 6-bisalkylamino-2-quinolinones," Bioorganic & Medicinal Chemistry Letters, 17:1527-1531.
Vinayak, Shaveta, et al., mTOR Inhibitors in the Treatment of Breast Cancer, Cancer Network, Oncology, pp. 1-12, Jan. 15, 2013.
Wang, Z. et al., (2007) "Anti-Inflammatory Properties and Regulatory Mechanism of a Novel Derivative of Artemisinin in Experimental Autoimmune Encephalomyelitis," J Immunol, 179:5958-5965.
Wei, L. et al., Pharmacological Targeting of Androgen Receptor Elicits Context-Specific Effects in Estrogen Receptor-Positive Breast Cancer, Cancer Res., 83(3):456-470, plus supplementary data sheet, (2023).
Wright, P., "Transdermal Drug Delivery Looks for New Frontiers," Pharmaceutical Commerce, Feb. 26, 2013.
Yardley, D. A, (2013) "Combining mTOR Inhibitors with Chemotherapy and Other Targeted Therapies in Advanced Breast Cancer: Rationale, Clinical Experience, and Future Directions," Breast Cancer: Basic and Clinical Research 7:7-22.
Yasui, Nobutaka, et al., Tumor Growth and Metastasis of human Colorectal Cancer Cell Lines I SCID Mice Resemble Clinical Metastatic Behaviors, Invasion & Metastasis 1997; 17:259-269, Karger AG.
Yu, Ziyang, et al., Selective Androgen Receptor Modulator RAD140 Inhibits the Growth of Androgen/Estrogen Receptor-Positive Breast Cancer Models with a Distinct Mechanism of Action, Clinical Cancer Research, 23(24) Dec. 15, 2017, pp. 7608-7620, Am Association for Cancer Research.
Zaytseva, Yekaterina Y. et al., MTOR Inhibitors in Cancer Therapy, Cancer Letters, 319 (2012) 1-7, Elsevier.
Zeng, C., et al., (2010) "Efficient Synthesis of (2R,3S)-2-amino-3-(benzyloxy)-4,4,4-trifluorobutanoic acid (4,4,4-trifluoro-OBn-D-allothreonine)," Tetrahedron Letters, 51 :5361-5363.
Zhang, X., et al., (2006) "Synthesis and SAR of Novel Hydantoin Derivatives as Selective Androgen Receptor Modulators," Bioorganic & Medicinal Chemistry Letters, 16:5763-5766.
Zhang, X., et al., (2007) "Design, Synthesis, and in Vivo SAR of a Novel Series of Pyrazolines as Potent Selective Androgen Receptor Modulators," J Med Chem, 50(16):3857-3869.
Zhang, Ying, et al., Inhibition of Peptide Acylation in PLGA Microspheres with Water-Soluble Divalent Cationic Salts, Pharmaceutical Research, vol. 26, No. 8, pp. 1986-1994, Aug. 2009, Springer Science + Business Media, LLC.
Zizic, T.M., et al., (2004) "Pharmacologic Prevention of Osteoporotic Fractures," Am Fam Physician, 70:1293-1300.

AR+BREAST CANCER TREATMENT METHODS

PRIORITY CLAIM

This application is a Continuation of U.S. patent application Ser. No. 16/696,110, filed on Nov. 26, 2019, issued as U.S. Pat. No. 11,771,682, which is a Continuation of U.S. patent application Ser. No. 15/628,559, filed on Jun. 20, 2017, now abandoned, which claims priority to U.S. Provisional Application No. 62/353,350, filed Jun. 22, 2016, U.S. Provisional Application No. 62/377,497, filed Aug. 19, 2016, and U.S. Provisional Application No. 62/461,546, filed Feb. 21, 2017, all of which are incorporated herein by reference in their entirety, including drawings.

BACKGROUND

The relationship between androgens and breast cancer has been recognized for some time. In the past, androgen therapy has been used for treating breast cancer in women with mixed success. As breast cancer rapidly evolves to develop resistance to antiestrogen hormonal treatments, there is an urgent need to develop new treatment of breast cancer.

SUMMARY OF THE INVENTION

In one aspect, the disclosure relates to methods for treating a subject (e.g., human) with breast cancer expressing the androgen receptor (AR+ breast cancer) through the administration of one or more AR agonist(s). In certain embodiments, the AR agonist is a selective androgen receptor modulator (SARM). In some embodiments, the breast cancers are positive for both the androgen receptor and the estrogen receptor (AR+/ER+). In certain embodiments of the methods disclosed herein, the breast cancers are positive for AR, ER and progesterone receptor (AR+/ER+/PR+). In certain embodiments, the breast cancers expressing AR do not test positive for Her2 (Her2⁻). In certain embodiments, the breast cancers comprise one or more mutations in the ER as disclosed herein. In certain embodiments, the one or more ER mutations affect the ability of the ligand binding domain of the ER to bind ligands having affinity to non-mutated ER (wild-type ER). In certain embodiments, the breast cancers initially positive for ER may lose tumor expression of ER. In certain embodiments, the subject is a premenopausal or postmenopausal woman. In certain embodiments, the SARM used for treating breast cancer is used in combination with a cell cyclin inhibitor and in some embodiments, the cell cyclin inhibitor is an inhibitor of CDK4 and/or CDK6 (CDK4/6 inhibitor). In certain embodiments, the SARM is used in combination with an mTOR inhibitor. In certain embodiments, the mTOR inhibitor is an inhibitor of mTOR2 and/or mTOR3. In some instances, the SARM is given by oral administration. In some embodiments, the cell cyclin inhibitor and/or mTOR inhibitor is given by oral administration. In certain embodiments the SARM and mTOR inhibitor or SARM and CDK4/6 inhibitor are combined together in a kit. In some embodiments, the SARM and mTOR inhibitor or SARM and CDK4/6 inhibitor are co-formulated.

In certain embodiments, the SARM is steroidal or non-steroidal and in certain embodiments the SARM is non-steroidal. In some embodiments, the SARM of this invention is selected from the group consisting of enobosarm, BMS-564929, LGD-4033, AC-262,356, JNJ-28330835, S-40503, LY-2452473 and GSK-2881078. In certain embodiments of the methods disclosed herein, the SARMs used according to the methods of this disclosure are described by the genus of compounds represented by Formula I and Formula IV as disclosed herein.

In some embodiments of the methods disclosed herein, the cell cyclin inhibitor is a CDK4/CDK6 inhibitor selected from the group consisting of palbociclib, ribociclib, trilaciclib and abemaciclib. In certain embodiments, the CDK4/CDK6 inhibitor is a compounds that inhibits both CDK4 and CDK6 with an $IC_{50}$<250 nM or <100 nM or <50 nM. In certain embodiments of the methods disclosed herein, the mTOR inhibitor (TORC1 and/or TORC2) is selected from the group consisting of sirolimus, temsirolimus, everolimus, ridaforolimus, and MLN0128. In certain embodiments, the methods of treating breast cancer using a combination of a SARM together with a PARP inhibitor and in some embodiments the PARP inhibitor is talazoparib, veliparib, niraparib, beigene290, E7449, KXO1, ABT767, CK102, JPI289, KX02, IMP4297, SC10914, NT125, PJ34, VPI289, ANG-3186 are disclosed. In certain embodiments, the methods of treating breast cancer using a combination of a SARM together with a BCL2 inhibitor are described and in some embodiments the BCL-2 inhibitor is venetoclax, navitoclax, ABT737, G3139 or S55746. In certain embodiments, the methods of treating breast cancer using a combination of a SARM together with an MCL1 inhibitor are described and in some embodiments the MCL-1 inhibitor is 7-(5-((4-(4-(N,N-Dimethylsulfamoyl)piperazin-1-yl)phenoxy)methyl)-1,3-dimethyl-1H-pyrazol-4-yl)-1-(2-morpholinoethyl)-3-(3-(naphthalen-1-yloxy)propyl)-1H-indole-2-carboxylic Acid, S63845, omacataxine, seliciclib, UMI-77, AT101, sabutoclax, TW-37. In particular embodiments, the methods of treating breast cancer using a combination of a SARM together with a PI3K inhibitor In some embodiments of the methods disclosed herein, the breast cancer is treatment naïve. In some embodiments, the breast cancer has not yet been treated with any endocrinological therapies. In certain embodiments of the methods disclosed herein, the breast cancer is resistant to at least one prior therapy. In some embodiments the prior treatment for which resistance has developed is an antiestrogen therapy, e.g., at least one of an aromatase inhibitor, a selective estrogen receptor modulator (SERM) or a selective estrogen receptor degrader (SERD). In certain embodiments, the subject (e.g., woman) is postmenopausal and has progressed on prior endocrine therapy, including, without limitation, SERDs (e.g., fulvestrant, RAD1901, AZD9496); SERMs (e.g., tamoxifen, toremifene), aromatase inhibitors, and combinations thereof. In some embodiments, the subject (e.g.woman) has metastatic breast cancer but has not yet been treated. In some embodiments, the subject (e.g.woman) has metastatic breast and has progressed after prior endocronological therapy. In some embodiments, the subject (e.g.woman) has metastatic breast and has progressed after treatment with a mTOR inhibitor, or a CDK4/6 inhibitor, or a PIK3 inhibitor.

Certain embodiments provide a method of treating breast cancer comprising the steps of measuring a baseline level of ZBTB16 mRNA expression or protein expression in an ER+/AR+ breast cancer subject, treating with an AR agonist or selective androgen receptor modulator as described herein, measuring the level of ZBTB16 (encoding protein PLZF) after the treatment, and if the ZBTB16 level after treatment has increased, continuing the treatment with the AR agonist or selective androgen receptor modulator. In certain embodiments, the subject is a woman, e.g., premenopausal or postmenopausal woman.

Also provided herein in some embodiments Isa diagnostic kit containing reagents for measuring the mRNA or protein expression of ZBTB16.

Provided herein is a method of identifying a subject who is likely to be responsive to the AR agonist therapy disclosed herein, comprising the steps of measuring a baseline level of ZBTB16 mRNA expression or protein expression, treating with an AR agonist (e.g., SARM) for a period of time comprising at least one administration, measuring the ZBTB16 mRNA expression level after the AR agonist therapy, and identifying the subject to be likely responsive to the AR agonist therapy if an increase in ZBTB16 mRNA expression has occurred. In some embodiments, the expression cut off to determine responsiveness is at least a x2 fold increase, a x4 fold increase; an x8 fold increase, a x10 fold increase; a x25 fold increase; a x50 fold increase or a >1×100 fold increase.

In certain embodiments, a method of treating a woman with breast cancer is provided wherein said woman expresses one or mutations in the estrogen receptor, for example, a mutation of ERα gene (ESR1). Such mutations can include fusion proteins where part of the estrogen receptor has been fused to part or all of another protein. In some embodiments, a method of treating a woman with breast cancer is provided wherein said woman is first evaluated for one or more of said mutations and/or fusions and if she tests positive for the one or more mutations and/or fusions, she is treated with an AR agonist, for example a SARM, either as a monotherapy or with one or more additional chemotherapeutics as described herein. In some embodiments, the subject expresses a mutated PI3K.

BRIEF DESCRIPTION OF DRAWINGS

FIG. 5A: Increase in ZBTB16 mRNA expression in RAD140 treatment of T47D breast cancer cells in vitro. FIG. 5B: Increase in ZBTB16 mRNA expression in RAD140 treatment of AR+/ER+ breast cancer in vivo (PDx #2).

DETAILED DESCRIPTION OF THE INVENTION

Figure 1:
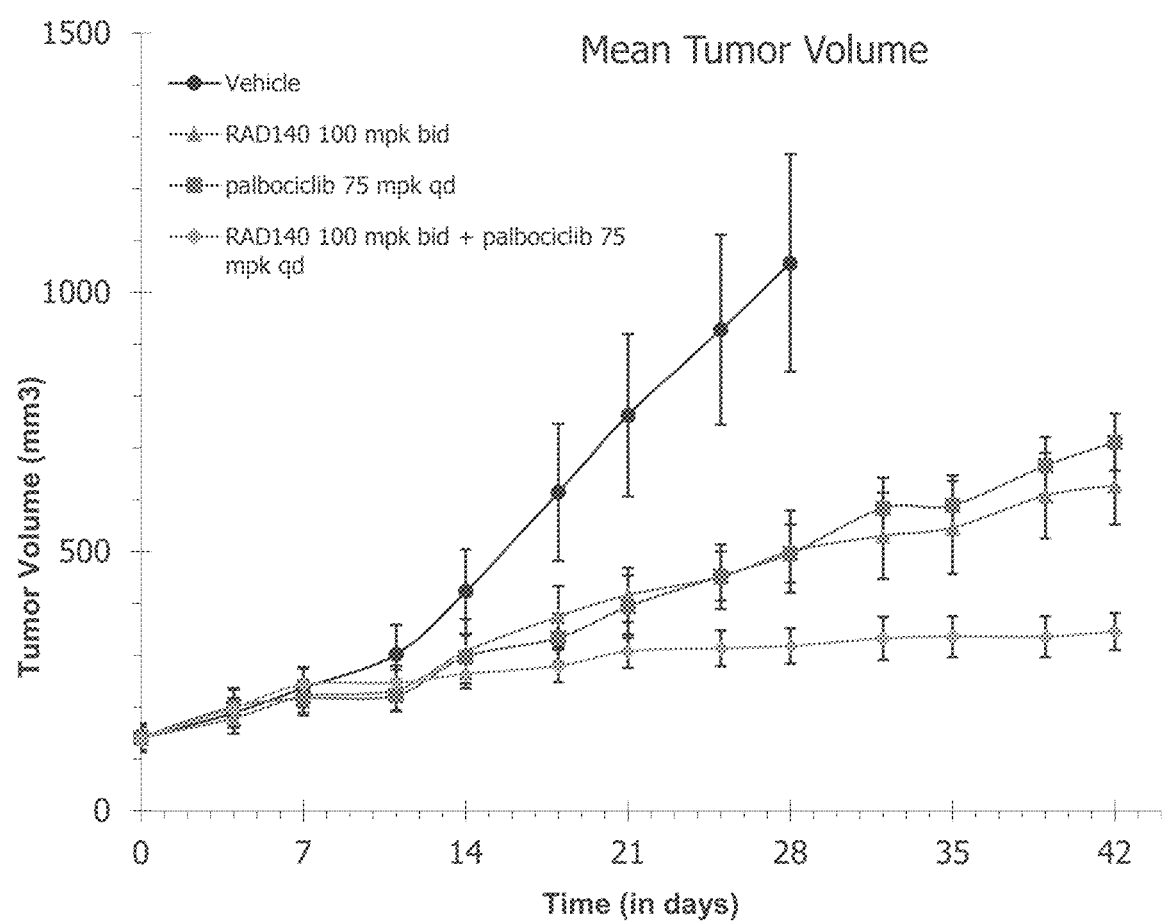
FIG. 1: Compound III ("RAD140") in combination with CDK inhibitor inhibited the growth of ER+/AR+ breast cancer in patient-derived xenograft (PDx) mice.

RAD140 is an orally available, nonsteroidal SARM with a distinct tissue selectivity profile. In vitro functional analysis showed that RAD140 is a potent AR agonist, comparable to dihydrotestosterone in breast cancer cells. As set forth in the Examples section below, a treatment of a SARM (e.g., RAD140) alone (Examples 3 and 4; Examples 7 and 8) or in combination with a CDK4/6 inhibitor (e.g., palbociclib in Examples 1 and 2) or an mTOR inhibitor (e.g., everolimus in Example 2) effectively inhibited the growth of ER+/AR+ breast cancer in multiple PDx and/or CDx mice. Molecular analysis of the xenograft tumor specimen revealed a substantial suppression of progesterone receptor (PR), consistent with previous reports on the crosstalk between AR and ER pathways (ER signaling upregulates PR), but also demonstrated potent activation of the AR pathway in RAD140 treated tumors. Furthermore, increase in ZBTB16 mRNA expression was observed in RAD140 treatment of AR+/ER+ breast cancer in vivo (PDx #2) and in vitro (T47D breast cancer cells); while PDx #2 treated with a SERD (fulvestrant) did not show appreciable induction of ZBTB16 mRNA expression (Example 5). A treatment of a SARM (e.g., RAD140) alone (Example 6) or in combination with a CDK4/6 inhibitor (e.g., palbociclib) effectively inhibited the growth of ER+/PR+/AR+/HER− breast cancer in WHIM18 PDx mice initially expressing the ESR-1 YAP fusion.

More specifically, RAD140 unexpectedly inhibited tumor growth in all four PDx models (PDx #1 (AR+/ER+/PR+/Her2−), PDx #2 (AR+/ER+), PDx #3 (AR+/ER+), and WHIM18 PDx (ER+/PR+/AR+/HER−)) and CDx models (ZR75 CDx derived from ZR-75-1 cancer cell line (AR+/ER+) (See examples).

RAD140 alone showed tumor growth inhibition (TGI) to ER+/PR+/AR+/HER− breast cancer in WHIM18 PDx which was highly resistant to the potent ER-degrader fulvestrant (Example 6). Unexpectedly, administration of RAD140 in combination with a CDK4/6 inhibitor (e.g., palbociclib) resulted in enhanced TGI effects than treatment of RAD140 or palbociclib alone. Furthermore, in PDx #1 (Example 1) and CDx (Example 2) models, the administration of RAD140 in combination with a CDK4/6 inhibitor (e.g., palbociclib) again unexpectedly resulted in enhanced TGI effects compared to treatment of RAD140 or palbociclib alone. In CDx (Example 2) models, the administration of RAD140 in combination with a mTOR inhibitor (e.g., everolimus) also resulted in enhanced TGI effects compared with treatment of RAD140 or palbociclib alone (Example 2). Thus, SARMs (e.g., RAD140) are likely to be an effective endocrine backbone that potentiates the TGI of AR+/ER+ and/or ER+/PR+/AR+/HER− cancer treatment, including endocrine resistant or less responsive to endocrine therapy (e.g., SERDs such as fulvestrant) and also strongly potentiate the activities of effective agents such as a cdk4/6 inhibitor, an m-TOR inhibitor, PI3k inhibitors, PARP inhibitors, BCL-2 inhibitors, MCL-1 inhibitors, or any combinations thereof.

Based on the results provided herein, methods are provided for treating AR+ tumor in a subject in need thereof by administering to the subject a therapeutically effective amount of an AR agonist (e.g., SARMs such as RAD140), or pharmaceutically acceptable salts or pharmaceutically acceptable solvates (e.g., hydrates) thereof. In certain embodiments, the methods further comprise administering to the subject a therapeutically effective amount of one or more second therapeutic agent(s) as described for herein, e.g., CDK4/6 inhibitors, mTOR inhibitors, PARP inhibitors, PIK3 inhibitors, BCL-2 inhibitors, and MCL-1 inhibitors.

Methods are also provided for treating breast cancer in a subject comprising the following steps:
- a) determining a baseline level of ZBTB16 mRNA and/or protein;
- b) administering an androgen receptor agonist;
- c) treating the subject with the AR agonist and then retesting the level of ZBTB16 mRNA and/or protein to provide a first level of ZBTB16 mRNA and/or protein; and
- d) continuing the administration of the AR agonist if the first level is higher than the baseline level of ZBTB16 mRNA and/or protein.

Examples of the subjects include, without limitation, mammals, e.g., human. In certain embodiments, the subjects for the methods disclosed herein are women, e.g., premenopausal women as well as postmenopausal women. In certain embodiments, the subjects for the methods disclosed herein have progressed on prior endocrine therapy, including, without limitation, SERDs (e.g., fulvestrant, RAD1901, AZD9496); SERMs (e.g., tamoxifen, toremifene), aromatase inhibitors (e.g. arimidex, letrozole, aromasin or combinations thereof, whether direct or sequential). In some embodiments, the subjects have metastatic breast cancer and have progressed on prior endocrine therapy (e.g., SERDs, SERMs, aromatase inhibitors, or combinations thereof). In certain embodiments, the subject (e.g.woman) has primary or metastatic breast cancer and has progressed on a cdk4/6 inhibitor, an mTOR inhibitor, or a PI3K inhibitor. In some embodiments, the woman has not been treated for breast cancer and an AR agonist (e.g., SARM) as described herein (e.g., RAD140) is administered, either alone or in combination with one of the other agents mentioned herein.

The presence of AR, ER, and/or PR in breast cancer tumor cells or tumor tissue can be readily evaluated, e.g., by immunohistochemistry (IHC). Certain embodiments of the methods disclosed herein further comprise determining the tumor expresses AR and optionally one or more other receptors (e.g., ER, PR, and Her2), especially ESR1. Moreover, the methods disclosed herein open up the door to new treatment regimens not depending on pathways likely to already have been treated into resistance (e.g., antiestrogen resistance).

Mutation of the ERα Gene (ESR1)

Resistance to hormonal therapy in ER+ breast cancer is often accompanied by various mutations in the estrogen receptor. In some instances, these mutated receptors result in increased resistance or even complete resistance to anti-estrogen/anti-endocrinological treatment when such resistance comes as a result of treatment with an aromatase inhibitor, an antiestrogen SERM such as tamoxifen or an estrogen receptor degrader (SERD) such as fulvestrant. While in some instances, the resistance to anti-estrogen treatment is accompanied by complete loss of estrogen receptor signaling through loss of the receptor itself, however, in many instances the mutated receptor still signals through the ER pathway. The reasons for antiestrogen resistance include examples where the estrogen receptor is mutated in a way where it shows reduced affinity for directly competitive ligands (i.e. Y537S ESR1, D538G) or that it loses part or all of its ligand binding domain (LBD) but still retains enough of other functional domains (e.g. DNA binding domain, AF1 domain and/or the hinge region) so that the receptor even when unbound by ligand (or unable even to bind ligand) retains constitutive activity meaning that the receptor effectively remains switched on. In some instances this occurs where chromosomal translocations occur resulting in gene fusion products where the ligand binding domain of the ER is truncated or deleted and another gene or partial gene substituted in its place resulting in a constitutively active receptor that does not require ligand binding. It has been demonstrated that tumor cells harboring such genetic alterations are resistant to therapeutic agents targeting ER LBD. Such mutant cells can be enriched over time. Also, it is known that some of the mutations pre-exist treatment with antiestrogens/SERDs/aromatase inhibitors. A subject expressing such receptors may be at greater risk of poor response to conventional anti-ER treatment but are excellent candidates for AR agonist or SARM therapy as described herein. Thus a patient may be a candidate for first line treatment or adjuvant treatment AR agonist or SARM when the subject expresses such a mutation or fusion. In certain embodiments, a subject is tested for expression of a candidate mutation or fusion to determine whether to treat her in a neoadjuvant, adjuvant or first line setting where she has not yet been treated with an endocrinological agent. The first line use of the SARM can be either as a monotherapy or in combination with at least one agent selected from the group consisting of CDK inhibitors (e.g., CDK 4/6 inhibitors), mTOR inhibitors (e.g., mTORc 1 and/or 2 inhibitors), PARP inhibitors, PIK3 inhibitors, BCL-2 inhibitors and MCL-1 inhibitors. Prior to the herein described methods, these mutations were particularly problematic as they foreclose treatment with antiestrogenic agents which are first line for ER+ breast cancer patients. As a result, the patients often proceed to cytotoxic agents and experience a course of their disease that is often accelerated and much harder to treat. It is an important aspect of this disclosure that AR agonists described herein can effectively treat subjects harboring such mutated ER.

In certain embodiments of the methods disclosed herein, the AR agonists disclosed herein are used to treat subjects having AR+/ER+ breast cancer that comprises one or more ER mutations. In certain embodiments, these mutations affect the ability of the ligand binding domain to bind ligands having affinity to non-mutated ER. In certain embodiments of this invention, said ER has one or more point mutations in the ligand binding domain that reduce or eliminate binding to normally binding ER ligands of the type agonists and/or antagonists including SERMs and SERDs, and in some instances have constitutive ER signaling activity, e.g., resistant to aromatase inhibitors as well. In certain embodiments, the mutated receptor has a ligand binding domain that is partially or completely absent. In some embodiments, said mutant receptor is a fusion receptor between a part of ESR1 and part or all of another protein. In certain embodiments, said mutant receptor is capable of signaling through ER pathways despite not being able to bind ligand or having an attenuated affinity for ligands that bind non-mutated ER. In some embodiments, the mutant or fusion retains the ER of DNA-binding domain function.

In certain embodiments of the methods disclosed herein, the subject expresses at least one specifically described ER-fusion gene. In one embodiment, the gene comprises an E545K mutation product in PIK3CA, an ESR1-AKAP12 fusion product, an ESR1-CCDC170 gene fusion product, an ESR1-YAP1 gene fusion product, an ESR1-POLH gene fusion product, an ESR1-PCDH11X gene fusion product, or combinations thereof. In a particular embodiment, the subject expresses an ESR1-YAP1 fusion. In certain embodiments, the subject has his/her first breast cancers or tumors evaluated to determine if the subject harbor one or more ER gene-fusion mutations in one or more samples of their cancer cells. If the subject does indeed harbor one or more of the described ER mutations, the subject is a candidate for treatment according to the compounds and methods of this invention. In some embodiments of this invention, the subject has already been treated with one or more prior therapies and in some embodiments the said prior therapy comprises an antiestrogen therapy utilizing, for example, an aromatase inhibitor, a SERM or a SERD. In some embodiments, the subject with the indicated mutation has not been pretreated at all for his/her breast cancer or has not been pre-treated with an antiestrogen. In certain embodiments, the subject has one or more of the mutations/fusions compromising ligand binding function or ESR1 activity.

In certain embodiments, the subject is initially positive for ER and then loses tumor expression of ER. In some embodiments, said lost expression occurred after the course of one or more prior treatments. In certain embodiments, said one or more prior treatments comprised treatment with an anti-estrogen further comprising one or more of an aromatase inhibitor, a SERM and a SERD. In certain embodiments, said subject who has lost ER expression in the tumor does express the progesterone receptor (PR).

In certain embodiments of the methods disclosed herein, the method disclosed herein further comprises a diagnostic step wherein said subject is first evaluated for one or more mutations/fusions as described herein. If the mutation/fusion is deemed to meet a predetermined cut off, the subject is a candidate for AR agonist/SARM treatment, either as a monotherapy or as a combination as described herein. In some embodiments, the mutant or fusion includes the ESR1-YAP fusion and/or closely related embodiments.

AR Agonists

Methods disclosed herein are not limited to any single class of compounds but rather include in the broadest scope, compounds that have affinity for the androgen receptor and can express at least some classic androgen activity, broadly thought of as AR agonists. One way to discern such activity preclinically, for example, is in a rat Herschberger assay where the effects of the prospective AR agonist are evaluated against a castrate background to determine if the compound has a stimulatory effect on androgen target tissues such as the levator ani, prostate and/or seminal vesicles. The AR agonists can be steroidal or non-steroidal, selective or not. In some embodiments, the AR agonist is a steroidal AR agonist such as testosterone (and esters thereof), DHT (and esters thereof), fluoxymesterone, oxandrolone, stanzolol, methandrostenelone, methyltestosterone, oxymetholone, nandrolone (and esters thereof). In certain embodiments, the AR agonists are SARMs (e.g., RAD140). In certain embodiments, SARMs demonstrate efficacy on tumor endpoints despite having reduced androgen drive on other tissues (e.g., prostate) or other expression profiles resulting in undesired outcomes such as virilization and hirsutism in females. In certain embodiments, SARMs often present with reduced drive on liver enzymes elevations and/or possibly deleterious changes in cholesterol levels such as decreased HDl and/or increased LDL. In certain embodiments, SARMs are non-steroidal and do not present the potential class liability of 17alpha alkylated steroids though they still have good oral activity in general. In certain embodiments, SARMs provide effective treatments that are less or non-virilizing. In certain embodiments, SARMs are not likely to feedback stimulate the central hormonal axis. In certain embodiments, SARMs (e.g., RAD140) can cross the blood brain barrier (the "BBB"). In certain embodiments, SARMs that can cross the BBB have suppressive effects on the central hormonal axis and decrease rather than increasing the ovarian production of sex steroids, e.g., estrogens such as estrone and estradiol as well as intracrine precursors such as DHEA, androstenedione, etc. In certain embodiments of the methods disclosed herein, the SARMs may be generally used for treating premenopausal women with breast cancer as well as postmenopausal women with breast cancer. In certain embodiments, suppressive SARMs (e.g., RAD140) provide additional CNS benefits in premenopausal or postmenopausal women having breast cancer. In certain embodiments, the AR agonists (e.g., SARMs) disclosed herein increase lean muscle mass and/or appetite. Thus, the AR agonists (e.g., SARMs) disclosed herein can be beneficial where a cancer cachexic state or wasting is a concern.

Not wishing to be bound by example, some of the SARMs contemplated in the methods disclosed herein include, without limitation, 2-chloro-4-[[(1R,2R)-2-hydroxy-2-methyl-cyclopentyl]amino]-3-methyl-benzonitrile (J Med Chem 2016; 59(2) 750), PF-06260414, enobosarm, BMS-564929, LGD-4033, AC-262356, JNJ-28330835, S-40503, GSK-2881078, RAD140, AZD-3514, MK4541, LG121071, GLPG0492, NEP28, YK11, MK0773, ACP-105, LY-2452473, S-101479, S-40542, S-42, LGD-3303 and the SARMs disclosed in U.S. Pat. Nos. 8,067,448 and 9,133,182, which are incorporated herein by reference. In addition, the SARMs suitable for methods disclosed herein include compounds according to Formula I disclosed herein (e.g., Compound II and Compound III), and compounds according to Formula IV disclosed herein, which may be used alone or in combination with one or more agents selected from the group consisting of CDK inhibitors (e.g. CDK4/6 inhibitors), mTOR inhibitors (e.g., mTORc 1 inhibitors and/or mTORc 2 inhibitors), PARP inhibitors, PIK3 inhibitors, BCL-2 inhibitors, MCL-1 inhibitors, and combinations thereof, for the treatment of AR+ breast cancer in a subject.

Compounds according to Formula I include compounds having the structure of Formula I

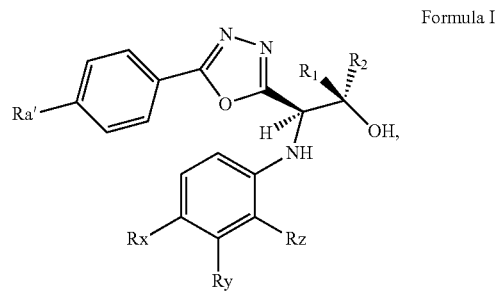

Formula I pharmaceutically acceptable salts thereof, and pharmaceutically acceptable solvates thereof, wherein:

$R_x$=CN;

$R_y$=CF$_3$ or Cl;

$R_z$=CH$_3$, CH$_2$CH$_3$ or Cl; or $R_y$ and $R_z$ together form:

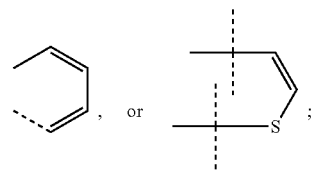

$R_{a'}$ is H, F, Cl, CN, OH or $OSO_3$; and $R_1$ and $R_2$ are each independently selected from hydrogen and methyl.

In certain embodiments, the compound according to Formula I is Compound II or Compound III (RAD140):

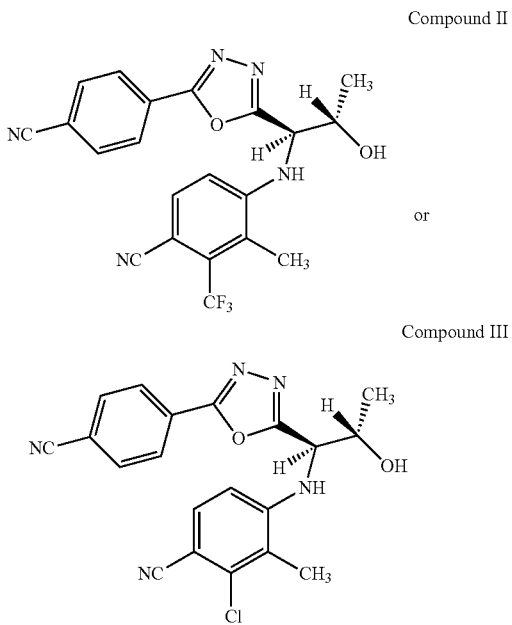

a pharmaceutically acceptable salt thereof, or pharmaceutically acceptable solvate thereof.

In certain embodiments, the compounds according to Formula IV include:

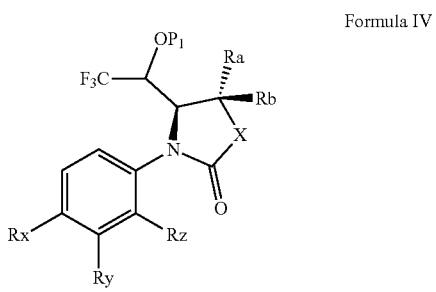

pharmaceutically acceptable salts thereof, and pharmaceutically acceptable solvates thereof, wherein:

$R_x$ is CN, Cl, Br, or $NO_2$;

$R_y$ is $CH_3$, $CF_3$, or halogen;

$R_z$ is hydrogen, optionally substituted $C_{1-3}$ alkyl, optionally substituted $C_{2-3}$ alkenyl, optionally substituted $C_{1-3}$ hydroxyalkyl, optionally substituted $C_{1-3}$ haloalkyl, $NO_2$, $NH_2$, OMe, halogen or OH;

$P_1$ is hydrogen or a metabolically labile group;

$R_a$ and $R_b$ are each independently hydrogen or $C_{1-3}$ alkyl; and

X is O.

Examples of optional substitution include, without limitation, 1-3 halogen atoms.

In certain embodiments, the SARM is a compound according to Formula IV, a pharmaceutically acceptable salt thereof, or pharmaceutically acceptable solvate thereof, wherein $R_x$ is CN.

In certain embodiments, the SARM is a compound according to Formula IV, a pharmaceutically acceptable salt thereof, or pharmaceutically acceptable solvate thereof, wherein $R_x$ is CN; $R_y$ is Cl or $CF_3$; $R_z$ is hydrogen, Cl or $CH_3$; $P_1$ is (C=O)—$C_{1-6}$ alkyl or hydrogen; and $R_a$ and $R_b$ are each independently hydrogen or —$CH_3$.

In certain embodiments, the SARM is a compound according to Formula IV, a pharmaceutically acceptable salt thereof, or pharmaceutically acceptable solvate thereof, wherein $R_x$ is CN; $R_y$ is Cl or $CF_3$; $R_z$ is hydrogen, Cl or $CH_3$; $P_1$ is (C=O)—$C_{1-6}$ alkyl or hydrogen; and $R_a$ and $R_b$ are both hydrogen.

Combination Therapy of AR Agonists and mTOR Inhibitors

The phosphoinositide 3-kinase (PI3K)/protein kinase B (AKT)/mammalian target of rapamycin (mTOR) pathway is an intracellular signaling pathway important in regulating the cell cycle. The frequent activation of the PI3K/AKT/mTOR pathway in cancer and its crucial role in cell growth and survival provide a challenge in finding an appropriate amount of proliferation versus differentiation in order to utilize this balance in the development of various therapies. See, e.g., Gitto et al., "Recent insights into the pathophysiology of mTOR pathway dysregulation," *Res. Rep. Bio.*, 2:1-16 (2015).

Inhibitors of the PI3K pathway have shown promises when given in combination with other therapies. For example, everolimus, as an allosteric mTOR inhibitor, was the first mTOR inhibitor approved in combination with AI exemestane (aromasin), for post-menopausal women with advanced hormone receptor positive (HR+), HER2– breast cancer (BOLERO-2 study) in 2012. Agents targeting other components of the PI3K pathway are under development for treating HR+ cancer, e.g., ATP-competitive, dual inhibitors of PI3K and mTOR (e.g., BEZ235, GDC-0980), pan-PI3K inhibitors which inhibit all four isoforms of class I PI3K (e.g., BKM120, GDC-0941), isoform-specific inhibitors of the various PI3K isoforms (e.g., BYL719, GDC-0032), allosteric and catalytic inhibitors of AKT (MK2206, GDC-0068, GSK2110183, GSK2141795, AZD5363), and ATP-competitive inhibitors of mTOR only (AZD2014, MLN0128, and CC-223). Dienstmann et al., "Picking the point of inhibition: a comparative review of PI3K/AKT/mTOR pathway inhibitors," *Mol. Cancer Ther.*, 13(5):1021-31 (2014).

Despite their great potential, undesirable side effects associated with mTOR inhibitors have hindered their development as effective cancer therapies. Kaplan et al., "Strategies for the management of adverse events associated with mTOR inhibitors," *Transplant Rev (Orlando)*, 28(3): 126-133 (2014); and Pallet et al., "Adverse events associated with mTOR inhibitors," *Expert Opin. Drug Saf* 12(2): 177-186 (2013).

Furthermore, there remains a need for more durable and effective targeted therapies that can overcome challenges associated with the current endocrine therapies, while providing additional benefits by combining with a second therapeutic agents (e.g., everolimus and other agents targeting the PI3K/AKT/mTOR pathway) to combat cancer in advanced stage and/or with resistance to prior treatments.

In some embodiments, the second therapeutic agent targets the PI3K/AKT/mTOR pathway and can be a mTOR inhibitor, a dual mTOR inhibitor, a PI3K/mTOR inhibitor, or an inhibitor of mTOR2 and/or mTOR3. In some embodiments, the second therapeutic agent is a rapamycin derivative (aka rapalog) such as rapamycin (sirolimus or rapamune, Pfizer), everolimus (Affinitor or RAD001, Novartis), ridaforolimus (AP23573 or MK-8669, Merck and ARIAD Pharmaceuticals), temsirolimus (Torisel or CCI779, Pfizer), including solvates (e.g., hydrates) and salts thereof. In some embodiments, the second therapeutic agent is a dual mTOR inhibitor that inhibits both mTORC1 and mTORC2, such as MLN0128, CC115 and CC223 (Celgene), OSI-027 (OSI Pharmaceuticals), and AZD8055 and AZD2014 (AstraZeneca), including solvates (e.g., hydrates) and salts thereof. In some embodiments, the second therapeutic agent is a PI3K/mTOR inhibitor such as GDC-0980, SAR245409 (XL765), LY3023414 (Eli Lilly), NVP-BEZ235 (Novartis), NVP-BGT226 (Novartis), SF1126, and PKI-587 (Pfizer), including solvates (e.g., hydrates) and salts thereof.

In certain embodiments, more than one of the second therapeutic agents disclosed above may be used in combination with AR agonists (e.g., SARMs) disclosed herein, e.g., compounds according to Formula I, compounds according to Formula IV, Compound II and Compound III. For example, an mTOR inhibitor can be used together with another mTOR inhibitor or with a PI3K/mTOR inhibitor. Also, it is known in the art that the second therapeutic agents disclosed above, including mTOR inhibitors, dual mTOR inhibitors, and PI3K/mTOR inhibitors, can be administered with other active agents to enhance the efficacy of the treatment for example can be used in combination with JAK2 inhibitors (Bogani et al., *PLOS One*, 8(1): e54826 (2013)), chemotherapy agents (Yardley, *Breast Cancer (Auckl)* 7: 7-22 (2013)). Accordingly, the second therapeutic agents also include these auxiliary active agents.

Figure 2:
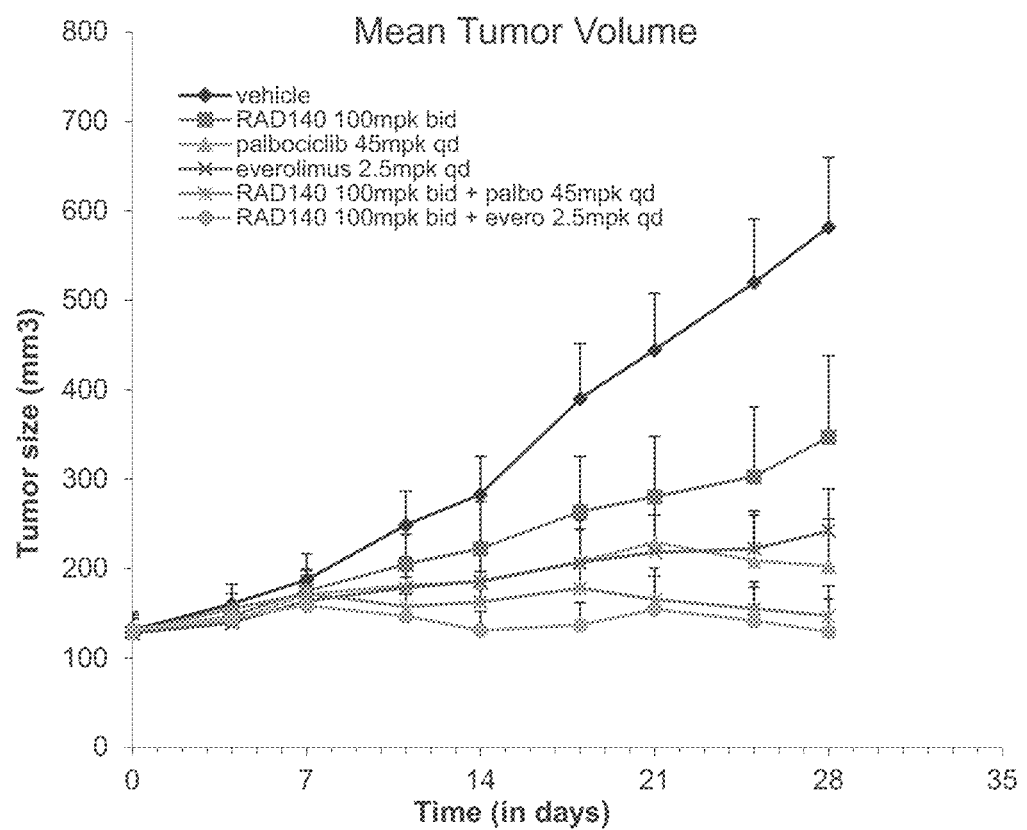
FIG. 2: Combined administration of RAD140 with CDK inhibitor or mTOR inhibitor inhibited the growth of ER+/AR+ breast cancer in cell line-derived xenograft (CDx) mice.

FIG. 2 illustrates the enhanced efficacy obtained when a mTOR inhibitor everolimus was used in combination with a SARM RAD140 in an in vivo model Combination Therapy of AR Agonists and CDK Inhibitors Cell cycle regulators such as cyclins and cyclin-dependent kinases (CDKs) have been reported to have effects on ER expression. Lamb et al., "Cell cycle regulators cyclin D1 and CDK4/6 have estrogen receptor-dependent divergent functions in breast cancer migration and stem cell-like activity," Cell Cycle 12(15): 2384-2394 (2013). Selective CDK4/6 inhibitors (e.g., ribociclib, abemaciclib and palbociclib) have enabled tumor types in which CDK4/6 has a pivotal role in the G1-to-S-phase cell cycle transition to be targeted with improved effectiveness and fewer adverse effects to normal cells. O'Leary et al., "Treating cancer with selective CDK4/6 inhibitors," *Nat. Rev. Clin. Oncol.* (2016), published online 31 Mar. 2016 (http://www.nature.com/nrclinonc/journal/vaop/ncurrent/full/nrclinonc.2016.26.html).

The selective CDK4/6 inhibitors demonstrated the best responses when tested in combination with ER-endocrine therapy in patients with ER-positive breast cancer. In this regard, it is helpful to keep in mind that AR pathways can intersect with ER pathways and possibly under some conditions, antagonize ER activity in a different manner than direct ER antagonism.

Palbociclib in combination with the aromatase inhibitor letrozole (PALoMA-1/TRIO 18 study) was approved for the treatment of hormone receptor (HR)-positive (HR+), HER2-negative (HER2−) advanced breast cancer as initial endocrine based therapy in postmenopausal women in February 2015. In February 2016, palbociclib in combination with the SERD fulvestrant (PALOMA-3 study) was approved for the treatment of ER+, HER2− advanced or metastatic breast cancer patients that had progressed on prior endocrine therapy. The FDA has granted the CDK4/6 inhibitor abemaciclib (LY2835219) a breakthrough therapy designation as monotherapy for heavily pretreated patients with refractory HR-positive advanced breast cancer, based on data from a phase I study (JPBA study). Additional combinations of selective CDK4/6 inhibitors (e.g., ribociclib, abemaciclib and palbociclib) with ER− endocrine therapies (e.g., AIs, SERMs and SERDs) are currently under development. However, it appears clinical or preclinical studies demonstrating the unexpected combined efficacy between SARMs and cdk4/6 inhibitors appear lacking until now.

Furthermore, CDK4/6 inhibitors demonstrate toxicities that may require intermittent therapy (O'Leary). Thus, there remains a need for effective and alternative combination-targeted therapies that can overcome challenges associated with the current endocrine therapies, while providing additional benefits by combining with CDK4/6 inhibitors to combat breast cancer, particularly in advanced stage and/or with resistance to prior treatments or with mutations identified as existing pre-prior therapy or after prior therapy that render the ESR1 target amenable to androgen intervention (including SARMs) where other endocrinological therapies are generally less effective or not effective at all, particularly those relying on a direct antiestrogenic effect such as an aromatase inhibitor, SERM or SERD.

In certain embodiments, the CDK4 and/or CDK6 inhibitors include, without limitation, palbociclib, abemaciclib, ribociclib and AMG925.

The in vivo illustration of this concept of an AR agonist (e.g., SARM) combined with a CDK4/CDK6 inhibitor (e.g., palbociclib) can be viewed in FIG. 1. As indicated in FIG. 1, the SARM RAD140 has very effective tumor suppressing capability, similar to a monotherapy with palbociclib. Unexpectedly, a combination therapy of RAD140 and palbociclib provided enhanced TGI compared to monotherapy with RAD140 or palbociclib. Thus, a combination therapy of AR agonists and CDK4/6 inhibitors may provide improved activity and marked clinical benefit for treatment of AR+ breast cancer. Similarly, FIG. 6 demonstrates efficacy alone or with palbociclib in the WHIM18 model initially expressing ESR1-YAP fusion where fulvestrant (as SERD) was ineffective alone and did not enhance the efficacy of palbociclib in the fulvestrant-palbociclib combination therapy.

Administration and Formulations

With regard to administration of the compounds and combinations according to the methods disclosed herein, the AR agonists (e.g., SARMs) or solvates or salts thereof and the CDK4 and/or CDK6 inhibitors (e.g., ribociclib, abemaciclib and palbociclib) or the mTOR inhibitors, PI3K inhibitors, PARP inhibitors, MCL-1 inhibitors and/or BCL2 inhibitors disclosed herein are administered in combination to a subject in need. The phrase "in combination" means that the AR agonists (e.g., SARMs) disclosed herein may be administered before, during, or after the administration of the CDK4 and/or CDK6 inhibitors or mTOR inhibitors, PI3K inhibitors, PARP inhibitors, MCL-1 inhibitors and/or BCL2 inhibitors. For example, the AR agonists (e.g., SARMs) and the CDK4 and/or CDK6 inhibitor or mTOR inhibitor, PI3K inhibitors, PARP inhibitors, MCL-1 inhibitors and/or BCL2 inhibitors can be administered in about one week apart, about 6 days apart, about 5 days apart, about 4 days apart, about 3 days apart, about 2 days apart, about 24 hours apart, about 23 hours apart, about 22 hours apart, about 21 hours apart, about 20 hours apart, about 19 hours apart, about 18 hours apart, about 17 hours apart, about 16 hours apart, about 15 hours apart, about 14 hours apart, about 13 hours apart, about 12 hours apart, about 11 hours apart, about 10 hours apart, about 9 hours apart, about 8 hours apart, about 7 hours apart, about 6 hours apart, about 5 hours apart, about 4 hours apart, about 3 hours apart, about 2 hours apart, about 1 hour apart, about 55 minutes apart, about 50 minutes apart, about 45 minutes apart, about 40 minutes apart, about 35 minutes apart, about 30 minutes apart, about 25 minutes apart, about 20 minutes apart, about 15 minutes apart, about 10 minutes apart, or about 5 minutes apart. In certain embodiments, the AR agonists (e.g., SARMs) and the CDK4 and/or CDK6 inhibitors or mTOR inhibitors, PI3K inhibitors, PARP inhibitors, MCL-1 inhibitors and/or BCL2 inhibitors are administered to the subject simultaneously or substantially simultaneously. In certain of these embodiments, the AR agonists (e.g., SARMs) and the CDK4 and/or CDK6 inhibitor (e.g., ribociclib, abemaciclib and palbociclib) or mTOR inhibitors (e.g., sirolimus, temsirolimus, everolimus, ridafarolimus and MLN0128), PI3K inhibitors, PARP inhibitors, MCL-1 inhibitors and/or BCL2 inhibitors disclosed herein may be administered as part of a single formulation. Included are kits where an AR agonist and one or more of the additional agents described herein are contained within a kit together, for example as a copackaging arrangement. By way of non-limiting example, kits containing RAD140 with a CDK4/6 inhibitor, m-TOR inhibitor, PI3K inhibitor, PARP inhibitor, MCL-1 inhibitor and/or BCL2 inhibitor such as those detailed herein are included within the scope.

In some embodiments, the combination of a single AR agonist (e.g., SARM) and a single CDK4 and/or CDK6 inhibitor or mTOR inhibitor, PI3K inhibitor, PARP inhibitor, MCL-1 inhibitor and/or BCL2 inhibitor is administered to a subject. In certain embodiments, the combination of one AR agonist (e.g., SARM) and a CDK4/CDK6 inhibitor and an mTOR inhibitor, PI3K inhibitor, PARP inhibitor, MCL-1 inhibitor and/or BCL2 inhibitor are administered together to a subject. Formulations of the AR agonists (e.g., SARMs) used in the methods disclosed herein have been generally disclosed in the literature and those teachings are herein incorporated by general reference. In particular, U.S. Pat. No. 8,067,448 discloses how to make the compounds and general formulation methods useful for formulating compounds according to Formula I, Compound II and Compound III and is herein incorporated by reference. Similarly, U.S. Pat. No. 9,133,182 discloses how to make the compounds according to Formula IV and formulate generally, and is herein incorporated by reference. In instances where specific formulation advice or direction is not available, some general principles to formulation may apply. For example, the compounds and combinations of the presently disclosed methods can be formulated into unit dosage forms, meaning physically discrete units suitable as unitary dosage for subjects undergoing treatment, with each unit containing a predetermined quantity of active material calculated to produce the desired therapeutic effect, optionally in association with a suitable pharmaceutical carrier. The unit dosage form can be for a single daily dose or one of multiple daily doses (e.g., about 1 to 4 or more times q.d.). When multiple daily doses are used, the unit dosage form can be the same or different for each dose. In certain embodiments, the compounds may be formulated for controlled release.

The compounds and combinations for use in the presently disclosed methods can be formulated according to any available conventional method. Examples of preferred dosage forms include a tablet, a powder, a subtle granule, a granule, a coated tablet, a capsule, a syrup, a troche, an inhalant, a suppository, an injectable, an ointment, an ophthalmic ointment, an eye drop, a nasal drop, an ear drop, a cataplasm, a lotion and the like. In the formulation, generally used additives such as a diluent, a binder, an disintegrant, a lubricant, a colorant, a flavoring agent, and if necessary, a stabilizer, an emulsifier, an absorption enhancer, a surfactant, a pH adjuster, an antiseptic, an antioxidant and the like can be used. In addition, the formulation is also carried out by combining compositions that are generally used as a raw material for pharmaceutical formulation, according to the conventional methods. Examples of these compositions include, for example, (1) an oil such as a soybean oil, a beef tallow and synthetic glyceride; (2) hydrocarbon such as liquid paraffin, squalane and solid paraffin; (3) ester oil such as octyldodecyl myristic acid and isopropyl myristic acid; (4) higher alcohol such as cetostearyl alcohol and behenyl alcohol; (5) a silicon resin; (6) a silicon oil; (7) a surfactant such as polyoxyethylene fatty acid ester, sorbitan fatty acid ester, glycerin fatty acid ester, polyoxyethylene sorbitan fatty acid ester, a solid polyoxyethylene castor oil and polyoxyethylene polyoxypropylene block co-polymer; (8) water soluble macromolecule such as hydroxyethyl cellulose, polyacrylic acid, carboxyvinyl polymer, polyethyleneglycol, polyvinylpyrrolidone and methylcellulose; (9) lower alcohol such as ethanol and isopropanol; (10) multivalent alcohol such as glycerin, propyleneglycol, dipropyleneglycol and sorbitol; (11) a sugar such as glucose and cane sugar; (12) an inorganic powder such as anhydrous silicic acid, aluminum magnesium silicicate and aluminum silicate; (13) purified water, and the like. Additives for use in the above formulations may include, for example, 1) lactose, corn starch, sucrose, glucose, mannitol, sorbitol, crystalline cellulose and silicon dioxide as the diluent; 2) polyvinyl alcohol, polyvinyl ether, methyl cellulose, ethyl cellulose, gum arabic, tragacanth, gelatine, shellac, hydroxypropyl cellulose, hydroxypropylmethyl cellulose, polyvinylpyrrolidone, polypropylene glycol-poly oxyethylene-block co-polymer, meglumine, calcium citrate, dextrin, pectin and the like as the binder; 3) starch, agar, gelatine powder, crystalline cellulose, calcium carbonate, sodium bicarbonate, calcium citrate, dextrin, pectic, carboxymethylcellulose/calcium and the like as the disintegrant; 4) magnesium stearate, talc, polyethyleneglycol, silica, condensed plant oil and the like as the lubricant; 5) any colorants whose addition is pharmaceutically acceptable is adequate as the colorant; 6) cocoa powder, menthol, aromatizer, peppermint oil, cinnamon powder as the flavoring agent; 7) antioxidants whose addition is pharmaceutically accepted such as ascorbic acid or alpha-tophenol.

The compounds and combinations for use in the presently disclosed methods can be formulated into a pharmaceutical composition as any one or more of the active compounds described herein and a physiologically acceptable carrier (also referred to as a pharmaceutically acceptable carrier or solution or diluent). Such carriers and solutions include pharmaceutically acceptable salts and solvates of compounds used in the methods of the instant invention, and mixtures comprising two or more of such compounds, pharmaceutically acceptable salts of the compounds and pharmaceutically acceptable solvates of the compounds. Such compositions are prepared in accordance with acceptable pharmaceutical procedures such as described in Remington's Pharmaceutical Sciences, 17th edition, ed. Alfonso R. Gennaro, Mack Publishing Company, Eaton, Pa. (1985), which is incorporated herein by reference.

The term "pharmaceutically acceptable carrier" refers to a carrier that does not cause an allergic reaction or other untoward effect in patients to whom it is administered and are compatible with the other ingredients in the formulation. Pharmaceutically acceptable carriers include, for example, pharmaceutical diluents, excipients or carriers suitably selected with respect to the intended form of administration, and consistent with conventional pharmaceutical practices. For example, solid carriers/diluents include, but are not limited to, a gum, a starch (e.g., corn starch, pregelatinized starch), a sugar (e.g., lactose, mannitol, sucrose, dextrose), a cellulosic material (e.g., microcrystalline cellulose), an acrylate (e.g., polymethylacrylate), calcium carbonate, magnesium oxide, talc, or mixtures thereof. Pharmaceutically acceptable carriers may further comprise minor amounts of auxiliary substances such as wetting or emulsifying agents, preservatives or buffers, which enhance the shelf life or effectiveness of the therapeutic agent.

The AR agonists (e.g., SARMs) and/or CDK4/6 inhibitor and/or mTOR inhibitors, PI3K inhibitors, PARP inhibitors, MCL-1 inhibitors and/or BCL2 inhibitors in a free form can be converted into a salt, if need be, by conventional methods. The term "salt" used herein is not limited as long as the salt is pharmacologically acceptable; preferred examples of salts include a hydrohalide salt (for instance, hydrochloride, hydrobromide, hydroiodide and the like), an inorganic acid salt (for instance, sulfate, nitrate, perchlorate, phosphate, carbonate, bicarbonate and the like), an organic carboxylate salt (for instance, acetate salt, maleate salt, tartrate salt, fumarate salt, citrate salt and the like), an organic sulfonate salt (for instance, methanesulfonate salt, ethanesulfonate salt, benzenesulfonate salt, toluenesulfonate salt, camphorsulfonate salt and the like), an amino acid salt (for instance, aspartate salt, glutamate salt and the like), a quaternary ammonium salt, an alkaline metal salt (for instance, sodium salt, potassium salt and the like), an alkaline earth metal salt (magnesium salt, calcium salt and the like) and the like. In addition, hydrochloride salt, sulfate salt, methanesulfonate salt, acetate salt and the like are preferred as "pharmacologically acceptable salt" of the compounds disclosed herein.

In certain embodiments, the AR agonists (e.g., SARMs) and CDK4/6 and/or mTOR inhibitors, PI3K inhibitors, PARP inhibitors, MCL-1 inhibitors and/or BCL2 inhibitors disclosed herein may be in a prodrug form, meaning that it must undergo some alteration (e.g., oxidation or hydrolysis) to achieve its active form.

The administration of the compounds and/or combinations disclosed herein can be by routes heretofore described for those compounds though in general such as transdermal, subcutaneously, intravenously, intranasally, pulmonary and oral. Oral is the preferred route for the combination methods of this invention.

A therapeutically effective amount of a combination of an AR agonist (e.g., SARM) and CDK4/6 inhibitor and/or mTOR inhibitor, PI3K inhibitor, PARP inhibitor, MCL-1 inhibitor and/or BCL2 inhibitor in the methods disclosed herein is an amount that, when administered over a particular time interval, results in achievement of one or more therapeutic benchmarks (e.g., slowing or halting of tumor growth, resulting in tumor regression, cessation of symptoms, etc.). The combination for use in the presently disclosed methods may be administered to a subject one time or multiple times. In those embodiments wherein the compounds are administered multiple times, they may be administered at a set interval, e.g., daily, every other day, weekly, or monthly. Alternatively, they can be administered at an irregular interval, for example on an as-needed basis based on symptoms, patient health, and the like. A therapeutically effective amount of the combination may be administered q.d. for one day, at least 2 days, at least 3 days, at least 4 days, at least 5 days, at least 6 days, at least 7 days, at least 10 days, or at least 15 days. Optionally, the status of the cancer or the regression of the tumor is monitored during or after the treatment, for example, by a FES-PET scan of the subject. The dosage of the combination administered to the subject can be increased or decreased depending on the status of the cancer or the regression of the tumor detected.

The skilled artisan can readily determine this amount, on either an individual subject basis (e.g., the amount of a compound necessary to achieve a particular therapeutic benchmark in the subject being treated) or a population basis (e.g., the amount of a compound necessary to achieve a particular therapeutic benchmark in the average subject from a given population). Ideally, the therapeutically effective amount does not exceed the maximum tolerated dosage at which 50% or more of treated subjects experience nausea, hirsutism, voice hoarsening or other more serious reactions that prevent further drug administrations. A therapeutically effective amount may vary for a subject depending on a variety of factors, including variety and extent of the symptoms, sex, age, body weight, or general health of the subject, administration mode and salt or solvate type, variation in susceptibility to the drug, the specific type of the disease, and the like. One means of demonstrating acute response to the present treatment regimens is to analyze progestin receptor expression. It has been discovered that the AR agonists (e.g., SARMs) used in the present methods lead to decreased expression of the progestin receptor indicating a response to the agent. Based on the extensive preclinical efficacy data in mouse xenografts presented in the examples, the calculation and disclosure of predicted effective human clinical doses for the SARM RAD140 is described in Example 9.

Examples of methods disclosed herein are for illustrative purposes and the invention is therefore not limited to the exemplified embodiments.

EXAMPLES

Example 1: SARM RAD140 in Combination with CDK Inhibitor Inhibited ER and AR Positive Breast Cancer Growth in PDx Mice(FIG. 1)

Material and Methods:

PDx model #1 maintained by a Contract Research Organization (CRO) was characterized as AR+/ER+/PR+/Her2− using IHC and gene chip microarray. Donor tumor slices were implanted subcutaneously into the flanks of intact female nude mice (n=7). Animals bearing tumors of sizes between 60-256 $mm^3$ were randomized into four treatment groups. Animals of each group received vehicle (circle, FIG. 1), RAD140 100 mg/kg twice a day (bid) (triangle, FIG. 1), palbociclib 75 mg/kg once a day (qd) (square, FIG. 1), or a combination of RAD140 100 mg/kg (bid) with palbociclib 75 mg/kg (qd) (diamond, FIG. 1), respectively. All test compounds were administered orally for 42 consecutive days. Tumor volume was measured twice weekly and % tumor growth inhibition (TGI) was calculated. Animals bearing tumors of size over 2,000 $mm^3$ were euthanized per animal welfare regulation. At the end of the study, plasma and tumor samples were collected for analyses of pharmacokinetics and pharmacodynamics. The mice were supplemented with estradiol added to their water in order to stimulate the growth of the tumors.

Results:

Treatment with RAD140 or palbociclib alone led to inhibition of tumor growth with approximately 53% TGI (tumor growth inhibition), respectively (FIG. 1). The combined administration of SARM and CDK4/6 inhibitor produced a TGI of 70% on day 28, at which point the number of animals in the vehicle-treated group dropped below 6 due to ethical termination of mice with larger tumors. The combination of RAD140 and palbociclib continued to exhibit potent tumor suppressive effect until the end of the study (day 42). The estimated endpoint TGI was higher than 70%. No appreciable degree of RAD140-treatment related weight loss was observed (data not shown).

In summary, the treatment with a SARM alone exhibited tumor inhibition comparable to that with palbociclib in AR+/ER+/PR+/Her2− breast cancer PDx-bearing mice. The combined administration of RAD140 with palbociclib produced enhanced growth inhibitory effect in these xenografts than RAD140 and palbociclib effected alone respectively. These results indicate combined administration of a SARM with or without a CDK4/6 inhibitor is efficacious in ER+/AR+ mammary tumors, and that a combination with a CDK4/6 enhanced TGI more than the SARM and CKD4/6 inhibitor could when administered alone respectively.

Example 2: Administration of SARM RAD140 in Combination with a CDK Inhibitor or an mTOR Inhibitor Inhibited ER and AR Positive Breast Cancer Growth in CDx Mice (Figure Material and Methods ZR-75-1 is a frequently used breast cancer cell line model that is ER+/AR+. The parental ZR-75-1 CDx model (ZR75 model) was established by injecting ZR-75-1 cells (donor tumors) into the flank of female nude mice. The ER+/AR+ status of these donor tumors were confirmed using immunoblotting (IB) and IHC. Donor tumor slices were implanted subcutaneously into the flanks of intact female nude mice (n=7). After randomnization of the established xenograft tumors, animals of each group received vehicle (diamond, FIG. 2), RAD140 100 mg/kg (bid) (square, FIG. 2), palbociclib 45 mg/kg (qd) (triangle, FIG. 2), a combination of RAD140 100 mg/kg (bid) with palbociclib 45 mg/kg (qd) (star, FIG. 2), everolimus 2.5 mg/kg (qd) ("X," FIG. 2), or a combination of RAD140 100 mg/kg (bid) with everolimus 2.5 mg/kg (qd) (circle, FIG. 2), respectively. All test compounds were administered orally for 28 consecutive days. The ZR75-1 xenograft tumors in animals were supported by estradiol pellets (0.18 mg 90 day release, Innovative Research America). Tumor volume was measured twice weekly and % TGI was calculated. Animals bearing tumors of size over 2,000 mm$^3$ were euthanized per animal welfare regulation. At the end of the study, plasma and tumor samples were collected for analyses of pharmacokinetics and pharmacodynamics.

Results:

Treatment with RAD140, palbociclib or everolimus alone led to inhibition of tumor growth with TGIs of 52%, 84%, or 75%, respectively (FIG. 2). The combination of RAD140 and palbociclib or everolimus exhibited potent tumor suppressive effect until the end of the study (day 28). The endpoint TGIs for RAD140-palbociclib combination and RAD140-everolimus combination were 96% and 101%, respectively. No appreciable degree of RAD140-treatment related weight loss was observed (data not shown).

In summary, the treatment with RAD140 alone exhibited anti-tumor activity in ER+/AR+ breast cancer CDx mice. The combined administration of RAD140 with either palbociclib or everolimus produced enhanced growth inhibitory effect in these xenografts than RAD140, palbociclib or everolimus alone, respectively. These results indicate a combined administration of the SARM RAD140 alone or in combination with either CDK4/6 inhibitor or mTOR is efficacious in ER+/AR+ mammary tumors.

Figure 3:
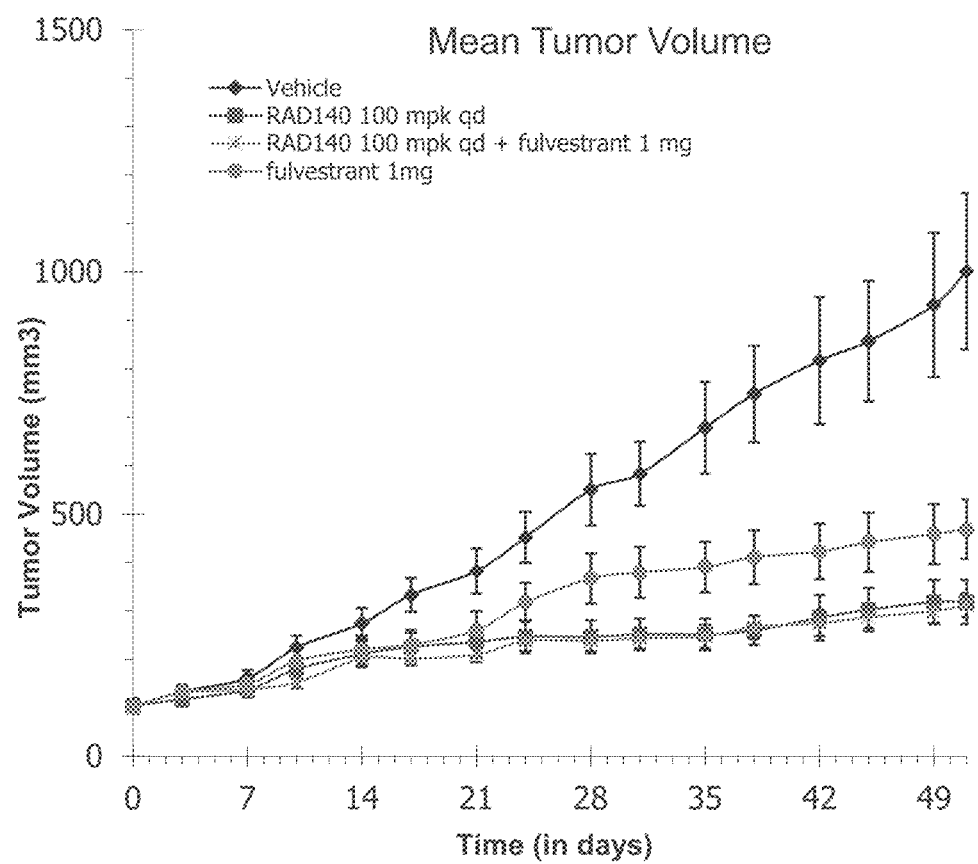
FIG. 3: RAD140 reduced the growth of ER+/AR+ breast cancer in PDx mice and was more efficacious than fulvestrant.

Example 3: SARM Reduced ER and AR Breast Cancer Growth in PDx Models and was More Effective than Fulvestrant (FIG. 3)

Material and Methods:

PDx model #2 maintained by a CRO was characterized as AR+/ER+ using IHC and gene chip microarray. Donor tumor slices were implanted subcutaneously into the flanks of intact female nude mice (n=10). After randomnization of the established xenografts, animals of each group received vehicle (diamond, FIG. 3), RAD140 100 mg/kg daily (qd) (square, FIG. 3), fulvestrant 1 mg weekly (qw) (circle, FIG. 3), or a combination of RAD140 100 mg/kg (qd) with fulvestrant 1 mg (qw) (star, FIG. 3), respectively. RAD140 was administered orally for 42 consecutive days and fulvestrant was administered subcutaneously once every week for 6 weeks. Tumor volume was measured twice weekly and % TGI was calculated. Animals bearing tumors of size over 2,000 mm$^3$ were euthanized per animal welfare regulation. The PDx models were supplemented with estradiol added to their water to stimulate the growth of the tumors. At the end of the study, plasma and tumor samples were collected for analyses of pharmacokinetics and pharmacodynamics.

Results:

Treatment with RAD140 alone led to inhibition of tumor growth with approximately 76% TGI (FIG. 3). Fulvestrant alone led to 59% TGI. The combined administration of RAD140 and fulvestrant produced a TGI of 76%, similar to that observed with RAD140 alone. No appreciable degree of SARM-treatment related weight loss was observed (data not shown).

In summary, SARM alone exhibited more effective anti-tumor activity than a SERD (e.g., fulvestrant, a standard-of-care drug for ER+ breast cancers). Combined administration of SARM and fulvestrant did not show improvement in efficacy in ER+/AR+ breast cancer PDx mice beyond what RAD140 demonstrated alone.

Figure 4:
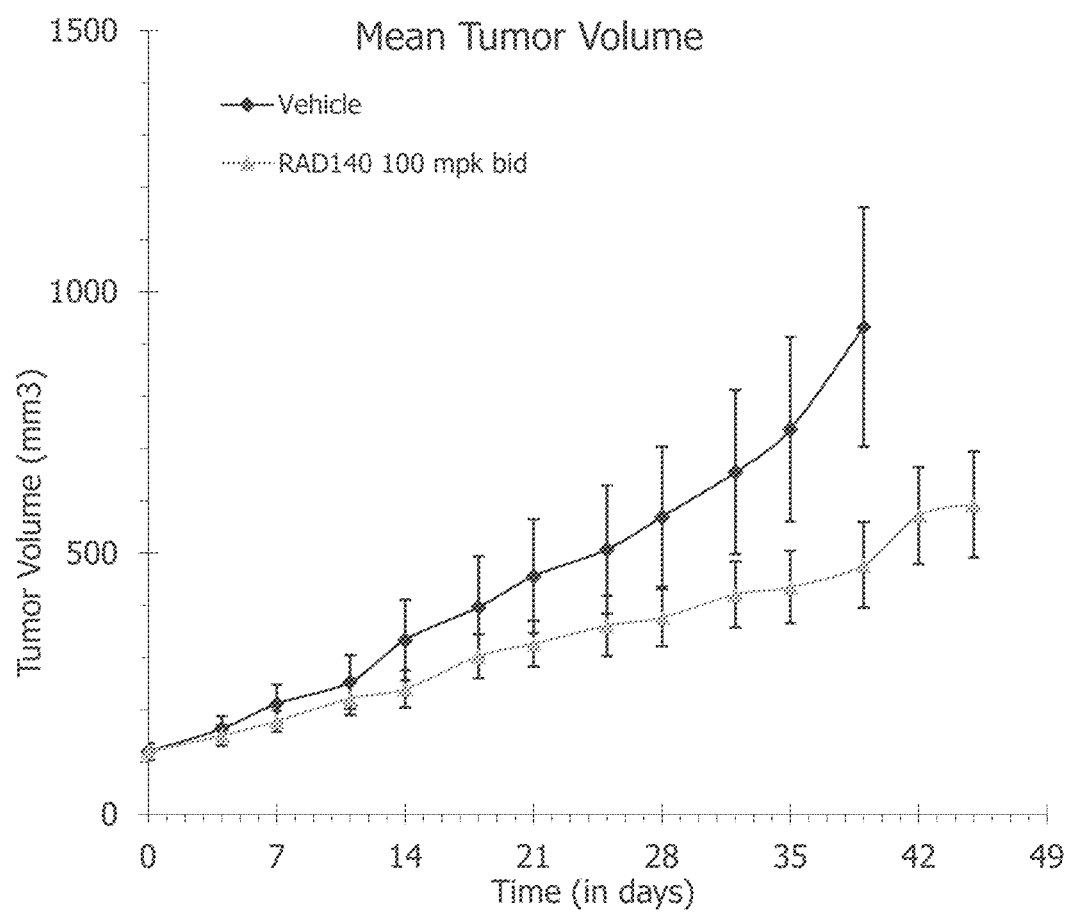
FIG. 4: RAD140 reduced the growth of ER+/AR+ breast cancer in PDx mice.

Example 4: RAD140 Reduced ER and AR Positive Breast Cancer Growth in PDx Models (FIG. 4)

Material and Methods:

PDx model #3 maintained by a CRO was characterized as AR+/ER+ using IHC and gene chip microarray. Donor tumor slices were implanted subcutaneously into the flanks of intact female nude mice (n=10). After randomization of the established xenografts, animals of each group received vehicle (diamond, FIG. 4) or RAD140 100 mg/kg (bid) (triangle, FIG. 4) for 45 days. The PDx mice were supplemented with estradiol added to their water in order to stimulate the growth of the tumors.

Results:

Treatment with RAD140 led to inhibition of tumor growth with 49% TGI (FIG. 4). No appreciable degree of RAD140-treatment related weight loss was observed (data not shown). In summary, these results indicates a SARM inhibits the growth of ER+/AR+ mammary tumors.

Figure 5A:
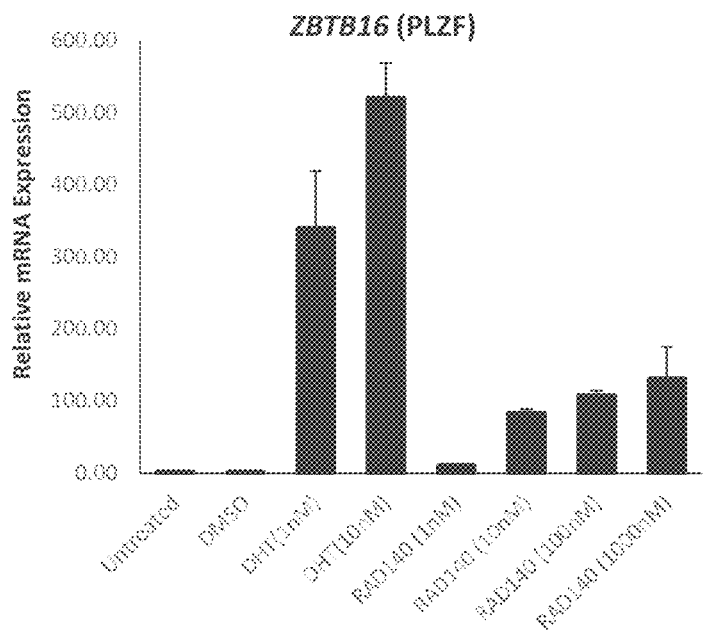
FIGS. 5A-5B: Increase in ZBTB16 mRNA expression in RAD140 treatment of breast cancer.

Example 5: RAD140 Induces AR Target Gene ZBTB16 Expression in ER+/AR+ Breast Cancer Cells and Patient-Derived Xenograft (PDx) (FIG. 5)

Material and Methods:

PDX model #2 was treated as described in Example 3 and frozen tumor samples collected 6 h after the last dose. T47D breast cancer cells positive for ER and AR were incubated in media supplemented with 5% charcoal-dextran stripped serum (CSS) for 48 h before treatment with vehicle (DMSO), RAD140 at 1 nM, 10 nM, 100 nM, 1,000 nM or DHT at 1 nM or 10 nM. Twenty-four hours after treatment, cells were harvested. RNA was extracted from the frozen tumor samples from PDX #2 and T47D cells mentioned above using a Qiagen RNeasy kit. Real-time quantitative PCR (qPCR) was performed using primer/probe sets for the AR target gene ZBTB16 (encoding PLZF protein) and GAPDH (internal control) (Applied Biosystems/Thermo-Scientific).

Figure 5B:
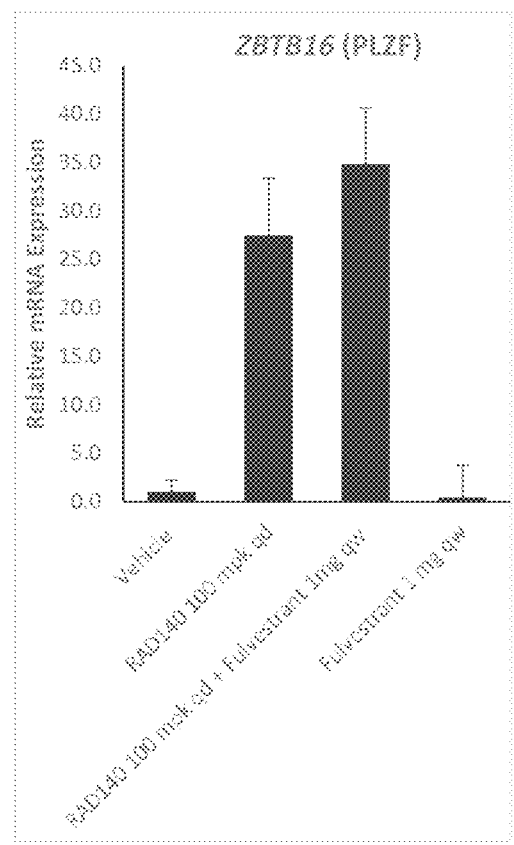

Results:

Treatment of T47D cells in vitro with RAD140 led to a dose dependent increase in ZBTB16 mRNA expression (FIG. 5A), with the 1,000 nM treatment leading to about 130-fold increase compared to that in vehicle treated cells. The natural androgen DHT also led to 300-500-fold induction of this gene. This further supports that RAD140 is a potent AR agonist. Consistently, in PDX #2 treated with RAD140 100 mg/kg (mpk) qd for 45 days, a ~25-fold induction of ZBTB16 gene was also seen compared to that in vehicle treated tumors (FIG. 5B). In contrast, fulvestrant, a SERD and antagonist of ER pathway, did not lead to appreciable increase in ZBTB16 gene expression (FIG. 5B). ZBTB16/PLZF has been implicated in prostate cancer as a tumor suppressor that is suppressed in recurrent tumors after androgen-deprivation therapy (ADT, aka castration). These results suggest the SARM RAD140 activated the transcription of AR target gene in breast cancer cells. More importantly, RAD140 suppressed breast cancer growth by inducing certain tumor suppressor genes including but not limited to ZBTB16/PLZF.

Example 6: RAD140 was Effective in the WHIM18 PDx Models with and without Palbociclib The WHIM18 PDx model is a patient derived xenograft of a breast cancer tumor transplanted into athymic female nude mice. The WHIM18 xenografts were ER+/PR+/AR+/HER− and grew independently of exogenous estrogen (e.g., 17β-estradiol). The WHIM18 PDx models were highly resistant to the potent ER-degrader fulvestrant. The WHIM18 PDx model harbored the ESR1-YAP1 fusion and an E545K mutation in PIK3CA.

The efficacy of RAD140 or fulvestrant alone and in combination with palbociclib in WHIM18 PDx models was evaluated for 56 days (8 weeks) of treatment. The primary endpoint was tumor growth. EDTA plasma and tumor tissues were collected after the last dose.

Materials and Methods

Female Outbred Athymic Nude Mice (The Jackson Laboratory 007850) (DOB 7-19-16) were implanted with a single cells suspension of 1.5×10$^6$ WHIM18 cells, passage 9. The cells were mixed 1:1 with DMEM:Matrigel (Corning REF 354234) in a total volume of 100 μl/mouse. Once tumors reached a mean volume of approximately 100-300 mm$^3$ (actual mean=179.9), 60 mice were randomized by tumor volume into 1 of 6 treatment groups (10 mice/group) using Biopticon's TumorManager™ software on day 62 post implantation of cells.

Each mouse was dosed by a dosage regimen described in Table 1 for 56 days: vehicle 0.5% carboxymethylcellulose (CMC, Sigma C4888), RAD140, or palbociclib were dosed by oral gavage once per day; fulvestrant was dosed by subcutaneous injection once every seven days. The dose volumes were calculated based on average weekly animal weight for each group as shown in Table 1. Prepared 0.5% CMC by dissolving 2.5 g in 400 ml warm sterile water, heat with stirring until dissolved, qs to 500 ml with sterile water stored at 4° C.

TABLE 1

Dosage regimens of WHIM18 PDx models

| Group # | Test Article | Dose | Dosing Route | Dosing Frequency |
|---|---|---|---|---|
| 1 (diamond, FIG. 6) | Vehicle (0.5% CMC) | | po | qd |
| 2 (square, FIG. 6) | RAD140 | 100 mg/kg | po | qd |
| 3 (triangle, FIG. 6) | Fulvestrant | 250 mg/kg | sc | q7D |
| 4 ("X," FIG. 6) | Palbociclib | 75 mg/kg | po | qd |
| 5 (star, FIG. 6) | RAD140 Palbociclib | 100 mg/kg 75 mg/kg | po po | qd qd |
| 6 (circle, FIG. 6) | Fulvestrant Palbociclib | 250 mg/kg 75 mg/kg | sc po | q7D qd |

The RAD140 composition for administration in this example was prepared by adding an appropriate amount of 0.5% CMC to RAD140 with continuous stirring at 4° C. while protected from light. The RAD140 composition was prepared weekly.

The palbociclib composition for administration in this example was prepared by adding an appropriate amount of sterile saline (0.9% Sodium Chloride for injection NDC 0409-7983-03) to palbociclib with stirring. The palbociclib composition was continuously stirred at 4° C. until palbociclib dissolved. The palbociclib composition was prepared weekly.

The tumor volumes were measured twice per week using Biopticon's TumorImager™ volumes were calculated using the corresponding TumorManager™ software. The mice were weighed once per week for the first half of the study (27 days). The mice were weighed twice per week once they showed weight loss. Additionally, any mouse with body weight loss (BWL) ≥5% compared to Day 0 or showed significant clinical signs (e.g., hunched posture, scruffy looking) was weighed daily. The dosing was suspended for any mice that had BWL≥15% compared to Day 0; and the dosing was resumed when the body weight of the mice restored to BWL ≤15%.

The mice were removed from the study if they became moribund, if their tumor volume exceeded 2,000 mm$^3$, or if they lost ≥20% of their body weight compared to Day 0. If possible, end of study samples were taken and the time of the last dose and take down time was recorded.

The remaining animals were taken down on day 56 approximately 6 hours following the last dose. The last dose of fulvestrant was given the morning of the takedown. The actual takedown was between 6-9 hours. Blood was collected via cardiac puncture immediately upon death via $CO_2$ and placed in EDTA tubes spun down at 2000 g for 10 minutes at 4° C. The plasma was transferred to Eppendorf tube and stored at −80° C.

Following the blood collection the tumors were excised and weighed. For each tumor, half of the tumor was placed in 10% Neutral Buffered Formalin (NBF), and the other half of the tumor was placed in an Eppendorf tube, flash frozen in liquid $N_2$, and then stored at −80° C. All tissue collected for formalin-fixed paraffin-embedded (FFPE) blocks were fixed in neutral buffered formalin (NBF) for 24-48 hours and then transferred to 70% ethanol before being shipped to be processed into FFPE blocks.

Figure 6:
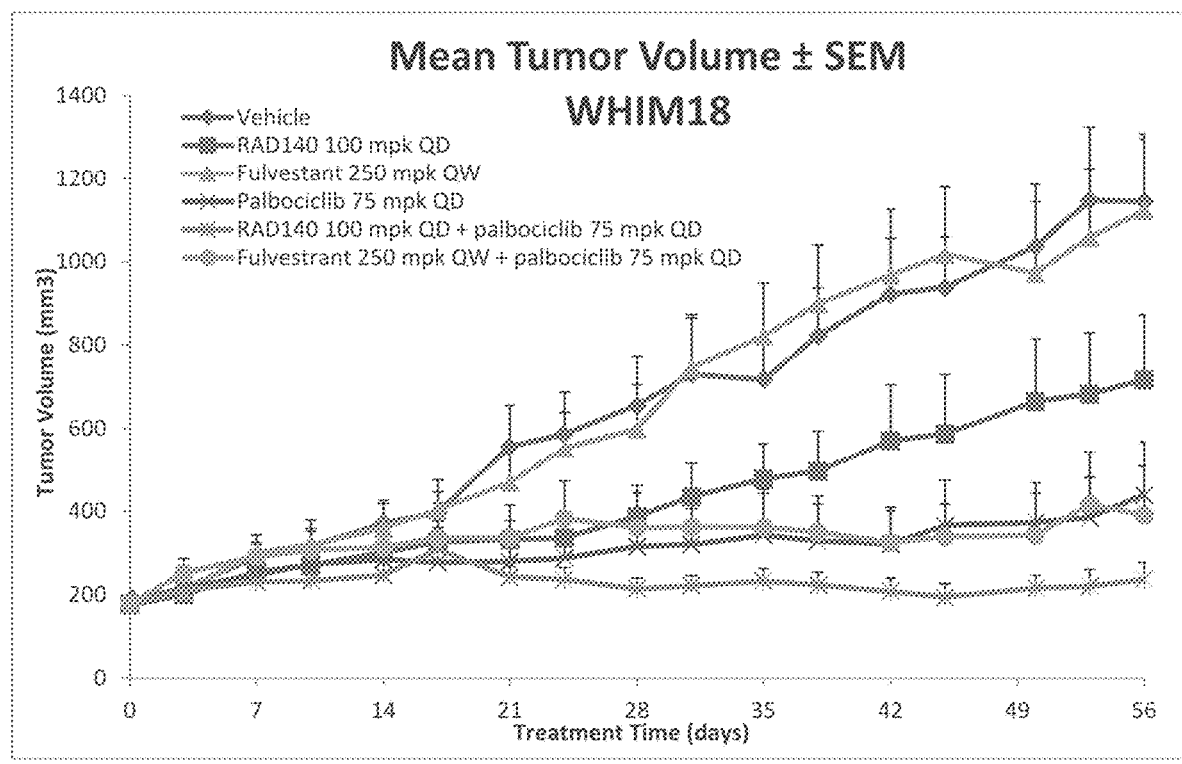
FIG. 6: Inhibition effects of RAD140, palbociclib, and a combination of RAD140 and palbociclib on the PDx tumor in WHIM 18 models harboring the ESR1-YAP1 fusion and an E545K mutation in PIK3CA.
Figure 7:
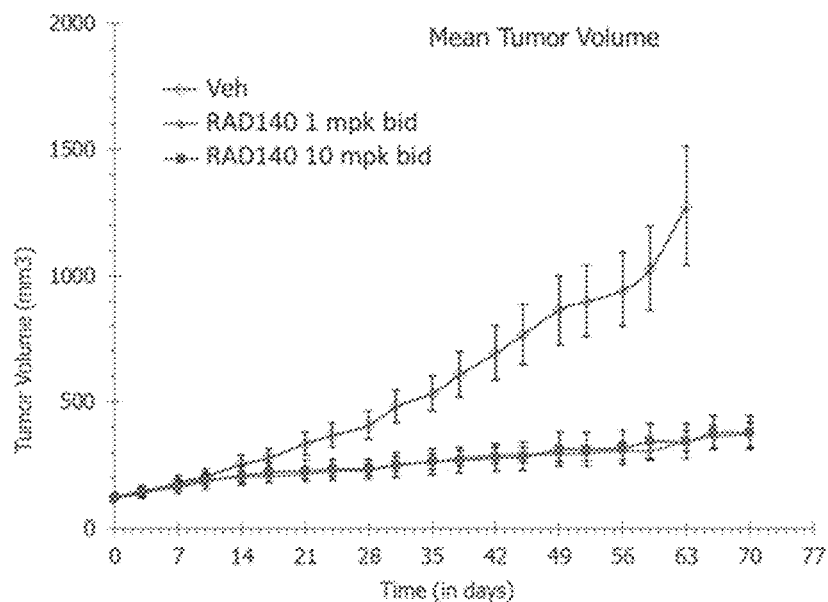
FIG. 7: RAD140 inhibited the growth of ER+/AR+ breast cancer patient-derived xenograft in the same PDX model as used in FIG. 3.
Figure 8:
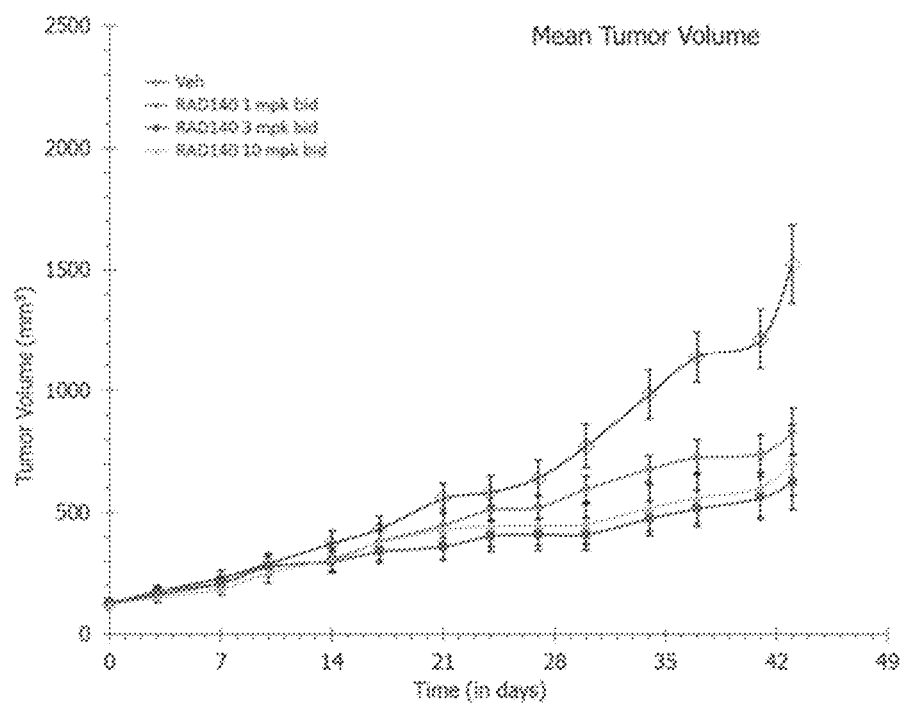
FIG. 8: RAD140 inhibited the growth of ER+/AR+ breast cancer patient-derived xenograft in the same model as used in FIG. 1.

Results:

The results of the in vivo experiment are shown graphically in FIG. 6. The relative reductions in tumor proliferation are shown with statistics below in Tables 2 and 3.

Tumor Growth Inhibition (TGI, in %) was calculated relative to the vehicle group on day 56 (Table 2, Formulation 1)

$$100 * \left\{ 1 - \left( \frac{\text{(Treatment Final Mean Volume} - \text{Treatment Baseline Mean Volume)}}{\text{(Vehical Final Mean Volume} - \text{Vehicle Baseline Mean Volume)}} \right) \right\} \quad \text{Formulation 1}$$

TABLE 2

% TGI of WHIM18 PDx models treated with RAD140, fulvestrant, palbociclib, RAD140 + Palbociclib and Fulvestrant + Palbociclib

| Group # | Test Article | % TGI |
|---|---|---|
| 1 (diamond, FIG. 6) | Vehicle (0.5% CMC) | — |
| 2 (square, FIG. 6) | RAD140 | 43.4 |
| 3 (triangle, FIG. 6) | Fulvestrant | 1.2 |
| 4 ("X," FIG. 6) | Palbociclib | 72.8 |
| 5 (star, FIG. 6) | RAD140 + Palbociclib | 94.1 |
| 6 (circle, FIG. 6) | Fulvestrant + Palbociclib | 77.8 |

Student's t-Test was calculated in excel using two-tailed distribution and two-sample equal variance of the delta tumor volume Day 56-Day 0.

TABLE 3 p values calculated from Student's t-Test of % TGI of WHIM18 PDx models treated with RAD140, fulvestrant, palbociclib, RAD140 + Palbociclib and Fulvestrant + Palbociclib

| Test Articles | p value |
|---|---|
| RAD140 vs Vehicle | 0.070 |
| Palbociclib vs Vehicle | 0.002 |
| Fulvestrant vs Vehicle | 0.933 |
| RAD140 vs Palbociclib | 0.165 |
| Fulvestrant + Palbociclib vs Vehicle | 0.001 |
| Fulvestrant + Palbociclib vs Fulvestrant | 0.004 |
| Fulvestrant + Palbociclib vs Palbociclib | 0.798 |

TABLE 3-continued p values calculated from Student's t-Test of % TGI of WHIM18 PDx models treated with RAD140, fulvestrant, palbociclib, RAD140 + Palbociclib and Fulvestrant + Palbociclib

| Test Articles | p value |
|---|---|
| RAD140 + Palbociclib vs Vehicle | 0.00001 |
| RAD140 + Palbociclib vs RAD140 | 0.006 |
| RAD140 + Palbociclib vs Palbociclib | 0.129 |

Administration of RAD140 at a dose of 100 mg/kg alone or in combination with palbociclib inhibited the growth of HER2−, ER+, PR+ breast cancer tumors implanted in female athymic nude mice (WHIM18 PDx) (FIG. 6). The combination of RAD140 with palbociclib appears to be more effective than either drug alone. No apparent toxicity was observed in any of the groups.

Example 7

In PDx model #2, i.e. the same PDx model as described in Example/FIG. 3, RAD140 administered at lower doses, 1 mg/kg bid, or 10 mg/kg bid both led to substantial inhibition of tumor growth, as judged by TGI values of ~81% in both groups.

Example 8

In PDx model #1, i.e. the same PDx model as described in Example/FIG. 1, RAD140 administered at lower doses, 1 mg/kg bid, 3 mg/kg bid or 10 mg/kg bid all led to substantial inhibition of tumor growth, as judged by TGI values of 49%, 65% and 57%, respectively.

Example 9

RAD140 was demonstrated to have good activity in a transplanted PDx tumor xenograft in nude mice. The activity was significant in a range from 1 mg/kg through 100 mg/kg. Taking into account the specific exposure levels in mice, and cross species pharmacokinetic modelling from both known and derived pharmacokinetic parameters, a dose range in women patients can be calculated. In particular, doses between 1 mg/kg (bid) and 100 mg/kg (bid) were all demonstrated to have good efficacy in one or more models described in the examples herein. Based on half life across speies and microsome stability, it is predicted that RAD140 will be effective as a once per day oral dosage with a dose range between 5 mg and 500 mg. For example, it is believed that the mouse efficacious dose of 10 mg/kg (qd) effectively translates to a dose of approximately 50 mg qd in a 60 kg woman. Since a range of 1 mg/kg to 100 mg/kg (bid) were shown effective, a broader range of 10 mg to 1000 mg is clinically relevant. In particular, within this range it can be seen that additional ranges of 10 mg-250 mg, 25 mg-250 mg, 25-500 are also supported. Similarly, individual dose points falling anywhere within the range are well supported such that any specific point within the range, integer or non-integer are supported. For example, doses like 12.5 mg, 17.5 mg and so on are specifically contemplated as are doses such as 10 mg, 25 mg, 50 mg, 75 mg, 100 mg, 150 mg, 200 mg, 300 mg, 400 mg, and 500 mg. By way of further non-limited examples, a dose of 10 mg, 15 mg, 20 mg, 25 mg, 50 mg, 75, 100, 125, 150, 175, 200, 250, 300, 350, 400, 450, 500 mg. QD dosing of the described doses are predicted to be quite adequate as RAD140 is predicted from pharmacokinetic studies in animals to have a long half life suitable for once daily dosing though bid dosing would also work BUT the doses given above for a single daily administration are divided in two since they would be given twice per day.

Example 10

Method 1: A method of treating AR+/ER+ breast cancer in a subject comprising administering to the subject a compound according to Formula I

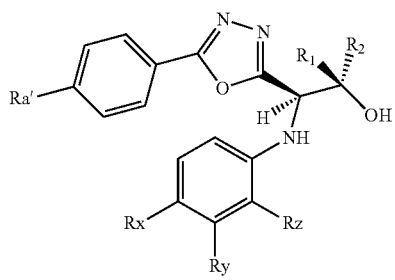

I a pharmaceutically acceptable salts thereof, or a pharmaceutically acceptable solvate thereof, wherein:

$R_x$=CN;
$R_y$=$CF_3$ or Cl;
$R_z$=$CH_3$, $CH_2CH_3$, or Cl; or
$R_y$ and $R_z$ together form:

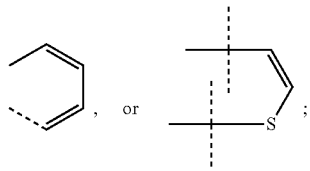

$R_{a'}$ is H, F, Cl, CN, OH or $OSO_3$—; and
$R_1$ and $R_2$ are each independently selected from the group consisting of hydrogen and methyl.

Method 2: The method according to method 1 wherein the compound according to Formula I is Compound II:

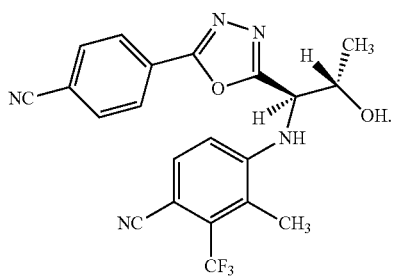

Compound II

Method 3. The method according to method 1 wherein the compound according to Formula I is RAD140 (Compound III):

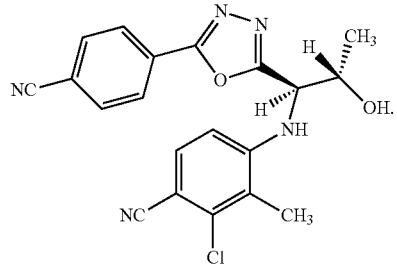

Compound III

Method 4. The method according to any one of methods 1-3 wherein the administration is via an oral route.

Method 5. The method according to any one of methods 1-4 wherein said subject is a woman.

Method 6. The method according to method 5 wherein said woman is a premenopausal woman.

Method 7. The method according to method 5 wherein said woman is a postmenopausal woman.

Method 8. The method of any one of methods 1-7 wherein the subject is treated in an adjuvant setting.

Method 9. The method of any one of methods 1-7 wherein the subject has had disease progression after treatment with one or more endocrinological agents.

Method 10. The method according to method 9 wherein said one or more endorinological agents are selected from the group consisting of SERMs, SERDs, progestins, aromatase inhibitors, and combinations thereof.

Method 11. The method of any one of methods 1-7 wherein said subject has had disease progression after treatment with one or more agents selected from the group consisting of CDK4/6 inhibitors, mTOR inhibitors, BCL-2 inhibitors, PI3K inhibitors, and combinations thereof.

Method 12. The method according to any one of methods 1-11 wherein said breast cancer is localized, advanced or metastatic breast cancer.

Method 13. The method according to any one of methods 3-12 wherein said RAD140 is dosed between 10 and 500 mg, 10 mg and 250 mg, or 25 mg and 250 mg per day.

Method 14. The method according to method 13 wherein the dose is once per day.

Method 15. The method according to any one of methods 1-14 wherein the subject expresses ESR1 comprising one or more mutations.

Method 16. The method according to method 15 wherein said mutation affects the binding affinity of ligands compared to non-mutated ESR1.

Method 17. The method according to method 16 wherein said mutation results in reduced estradiol affinity for the mutated ESR1 compared to the non-mutated ESR1.

Method 18. The method according to any one of methods 15-17 wherein said mutation signals ligand dependently or ligand independently through the ESR1 pathway.

Method 19. The method according to any one of methods 15-18 wherein said mutation results in a fusion protein containing at least 10 continuous amino acids from a sequence of a non-mutated ESR1 and at least 10 continuous amino acids from another human protein.

Method 20. The method according to any one of methods 15-19 wherein said mutation results in ESR1 missing 10 or more consecutive amino acids from its normal (non-mutated) ligand binding domain amino acid sequence.

Method 21. The method according to any one of methods 15-20 wherein said mutation comprises one or more mutations selected from the group consisting of ESR1-AKAP12, ESR1-CCDC170, ESR1-YAP1, ESR1-POLH, ESR1-PCDH11X, and combinations thereof.

Method 22. The method according to any one of methods 1-21 wherein the treatment further comprises the administration of a CDK4/6 inhibitor.

Method 23. The method according to method 22 wherein said CDK4/6 inhibitor has an $IC_{50}$ of <100 nM against CDK4 and CDK6.

Method 24. The method according to any one of methods 1-23 wherein said CDK4/6 inhibitor is selected from the group consisting of palbociclib, ribociclib, trilaciclib and abemaciclib.

Method 25. The method according to any one of methods 1-21 wherein said treatment further comprises the administration of an mTOR inhibitor.

Method 26. The method of method 25 wherein said mTOR inhibitor is selected from the group consisting of sirolimus, temsirolimus, everolimus, ridafarolimus, and MLN0128.

Method 27. The method of any one of methods 1-21 further comprising the administration of a PI3K inhibitor.

Method 28. The method of method 27 wherein said PI3K inhibitor is BEZ235, GDC-0980, BKM120, GDC-0941, BYL719, GDC-0032, MK2206, GDC-0068, GSK2110183, GSK2141795, AZD5363, AZD2014, MLN0128 or CC-223.

Method 29. The method according to any one of methods 1-21 further comprising the administration of a PARP inhibitor.

Method 30. The method of method 29 wherein said PARP inhibitor is talazoparib, veliparib, niraparib, beigene290, E7449, KX01, ABT767, CK102, JPI289, KX02, IMP4297, SC10914, NT125, PJ34, VPI289 or ANG-3186.

Method 31. The method according to any one of methods 1-21 further comprising the administration of a MCL-1 inhibitor.

Method 32. The method according to method 31 wherein said MCL-1 inhibitor is 7-(5-((4-(4-(N,N-Dimethylsulfamoyl)piperazin-1-yl)phenoxy)methyl)-1,3-dimethyl-1H-pyrazol-4-yl)-1-(2-morpholinoethyl)-3-(3-(naphthalen-1-yloxy)propyl)-1H-indole-2-carboxylic Acid, S63845, omacataxine, seliciclib, UMI-77, AT101, sabutoclax or TW-37.

Method 33. The method according to any one of methods 1-21 further comprising the administration of a BCL-2 inhibitor.

Method 34. The method of method 33 wherein said BCL-2 inhibitor is venetoclax, navitoclax, ABT737, G3139 or S55746.

Method 35. The method according to any one of methods 1-7 or 12-34 wherein said treating is first line treatment in a non-adjuvant setting.

Method 36. A kit comprising an AR agonist according to any one of methods 1-3 and one or more agents selected from the group consisting of PARP inhibitors, mTOR inhibitors, CDK4/6 inhibitors, PI3K inhibitors, BCL2 inhibitors, MCL-1 inhibitors, and combinations thereof.

Method 37. A method of treating AR+/ER+ breast cancer in a subject comprising the administration of a steroidal or non-steroidal AR agonist together with one or more agents selected from the group consisting of mTOR inhibitors, CDK4/6 inhibitors, PI3K inhibitors, PARP inhibitors, BCL2 inhibitors, MCL-1 inhibitors, and combinations thereof.

Method 38. The method of method 37 wherein said AR agonist is a steroidal AR agonist.

Method 39. The method according to method 38 wherein said AR agonist is a selective androgen receptor modulator.

Method 40. The method according to method 39 wherein said selective androgen receptor modulator is selected from the group consisting of 2-chloro-4-[[(1R,2R)-2-hydroxy-2-methyl-cyclopentyl]amino]-3-methyl-benzonitrile, PF-06260414, enobosarm, BMS-564929, LGD-4033, AC-262356, JNJ-28330835, S-40503, GSK-2881078, AZD-3514, MK4541, LG121071, GLPG0492, NEP28, YK11, MK0773, ACP-105, LY-2452473, S-101479, S-40542, S-42 and LGD-3303.

Method 41. The method according to any one of methods 37-40 wherein the treatment is in an adjuvant setting.

Method 42. The method according to any one of methods 37-40 wherein said treating is first line in a non-adjuvant setting.

Method 43. The method according to any one of methods 37-40 wherein said subject has had disease progression after treatment with a prior endocrinological therapy.

Method 44. The method according to any one of methods 37-40 or method 43 wherein said subject has had disease progression after treatment with an agent selected from the group consisting of mTOR inhibitors, CDK4/6 inhibitors, PI3K inhibitors, PARP inhibitors, BCL2 inhibitors, MCL-1 inhibitors, and combinations thereof.

Method 45. The method according to any one of methods 37-44 wherein said subject is a woman.

Method 46. The method of method 45 wherein said woman is a premenopausal woman.

Method 47. The method according to method 45 wherein said woman is a post-menopausal woman.

Method 48. The method according to any one of methods 37-47 wherein said breast cancer is localized.

Method 49. The method according to any one of methods 37-47 wherein said breast cancer is advanced or metastatic.

Method 50. The method according to any one of methods 37-49 wherein said m-TOR inhibitor is sirolimus, temsirolimus, everolimus, ridafarolimus or MLN0128.

Method 51. The method according to any one of methods 37-50 wherein said CDK4/6 inhibitor is palbociclib, ribociclib, trilaciclib or abemaciclib.

Method 52. The method according to any one of methods 37-51 wherein said PI3K inhibitor is BEZ235, GDC-0980, BKM120, GDC-0941, BYL719, GDC-0032, MK2206, GDC-0068, GSK2110183, GSK2141795, AZD5363, AZD2014, MLN0128 or CC-223.

Method 53. The method according to any one of methods 37-52 wherein said PARP inhibitor is talazoparib, veliparib, niraparib, beigene290, E7449, KX01, ABT767, CK102, JPI289, KX02, IMP4297, SC10914, NT125, PJ34, VPI289 or ANG-3186.

Method 54. The method according to any one of methods 37-53 wherein said MCL-1 inhibitor is 7-(5-((4-(4-(N,N-Dimethylsulfamoyl)piperazin-1-yl)phenoxy)methyl)-1,3-dimethyl-1H-pyrazol-4-yl)-1-(2-morpholinoethyl)-3-(3-(naphthalen-1-yloxy)propyl)-1H-indole-2-carboxylic Acid, S63845, omacataxine, seliciclib, UMI-77, AT101, sabutoclax or TW-37.

Method 55. The method according to any one of methods 37-54 wherein said BCL-2 inhibitor is venetoclax, navitoclax, ABT737, G3139 or S55746.

Method 56. The method according to any one of methods 37-55 wherein the active agents are administered together.

Method 57. The method according to any one of methods 35-56 wherein the active agents are administered in a coformulation.

Method 58. A kit useful for treating breast cancer comprising an AR agonist or selective androgen receptor modulator, and one or more agents selected from the group consisting of mTOR inhibitors, CDK4/6 inhibitors, PI3K inhibitors, PARP inhibitors, BCL2 inhibitors, MCL-1 inhibitors, and combinations thereof.

Method 59. A method of treating AR+/ER+ breast cancer in a subject wherein said subject harbors one or more ESR1mutations, said method comprising the administration of an AR agonist.

Method 60. The method of method 59 wherein said AR agonist is non-steroidal.

Method 61. The method of method 60 wherein said AR agonist is a selective androgen receptor modulator.

Method 62. The method according to method 61 wherein said selective androgen receptor modulator is selected from the group consisting of 2-chloro-4-[[(1R,2R)-2-hydroxy-2-methyl-cyclopentyl]amino]-3-methyl-benzonitrile, PF-06260414, enobosarm, BMS-564929, LGD-4033, AC-262356, JNJ-28330835, 5-40503, GSK-2881078, AZD-3514, MK4541, LG121071, GLPG0492, NEP28, YK11, MK0773, ACP-105, LY-2452473, 5-101479, 5-40542, S-42 and LGD-3303.

Method 63. The method according to any of methods 58-62 wherein said mutation affects the binding affinity of ligands compared to non-mutated ESR1.

Method 64. The method according to any one of methods 59-63 wherein said mutation results in reduced estradiol affinity for the mutated ESR1 compared to the non-mutated ESR1.

Method 65. The method according to any one of methods 59-64 wherein said mutation signals ligand dependently or ligand independently through the ESR1 pathway.

Method 66. The method according to any one of methods 59-65 wherein said mutation results in a fusion protein containing at least 10 continuous amino acids from a sequence of a non-mutated ESR1 and at least 10 continuous amino acids from another human protein.

Method 67. The method according to any one of methods 59-66 wherein said mutation results in ESR1 missing 10 or more consecutive amino acids from its normal (non-mutated) ligand binding domain amino acid sequence.

Method 68. The method according to any one of methods 59-67 wherein said mutation is a fusion selected from the group consisting of ESR1-AKAP12, ESR1-CCDCl70, ESR1-YAP1, ESR1-POLH, ESR1-PCDH1IX, and combinations thereof.

Method 69. The method according to any one of methods 59-68 wherein the administration is via an oral route.

Method 70. The method according to any one of methods 59-69 wherein said treating is in an adjuvant setting.

Method 71. The method according to any one of methods 59-69 wherein said treating is first line in a non-adjuvant setting.

Method 72. The method according to any one of methods 59-69 wherein said subject has had disease progression after treatment with a prior endocrinological therapy.

Method 73. The method according to any one of methods 59-69 or 72 wherein said subject has had disease progression after treatment with one or more agents selected from the group consisting of mTOR inhibitors, CDK4/6 inhibitors, PI3K inhibitors, PARP inhibitors, BCL2 inhibitors, MCL-1 inhibitors, and combinations thereof.

Method 74. The method according to any one of methods 59-73 wherein said subject is a woman.

Method 75. The method of method 74 wherein said woman is a premenopausal woman.

Method 76. The method according to method 74 wherein said woman is a post-menopausal woman.

Method 77. The method according to any one of methods 59-76 wherein said breast cancer is localized.

Method 78. The method according to any one of methods 59-76 wherein said breast cancer is advanced or metastatic.

Method 79. The method according to any one of methods 59-78 wherein the treatment further comprises the administration of a CDK4/6 inhibitor.

Method 80. The method according to method 79 wherein said CDK4/6 inhibitor has an $IC_{50}$ of <100 nM against CDK4 and CDK6.

Method 81. The method according to method 79 wherein said CDK4/6 inhibitor is selected from the group consisting of palbociclib, ribociclib, trilaciclib and abemaciclib.

Method 82. The method according to any one of methods 59-78 wherein said treatment further comprises the administration of an mTOR inhibitor.

Method 83. The method according to method 82 wherein said mTOR inhibitor is selected from the group consisting of sirolimus, temsirolimus, everolimus, ridafarolimus, and MLN0128.

Method 84. The method of any one of methods 59-78 further comprising the administration of a PI3K inhibitor.

Method 85. The method of method 84 wherein said PI3K inhibitor is BEZ235, GDC-0980, BKM120, GDC-0941, BYL719, GDC-0032, MK2206, GDC-0068, GSK2110183, GSK2141795, AZD5363, AZD2014, MLN0128 or CC-223.

Method 86. The method according to any one of methods 59-78 further comprising the administration of a PARP inhibitor.

Method 87. The method of method 86 wherein said PARP inhibitor is talazoparib, veliparib, niraparib, beigene290, E7449, KX01, ABT767, CK102, JPI289, KX02, IMP4297, SC10914, NT125, PJ34, VPI289 or ANG-3186.

Method 88. The method according to any one of methods 59-78 further comprising the administration of a MCL-1 inhibitor.

Method 89. The method according to method 88 wherein said MCL-1 inhibitor is 7-(5-((4-(4-(N,N-Dimethylsulfamoyl)piperazin-1-yl)phenoxy)methyl)-1,3-dimethyl-1H-pyrazol-4-yl)-1-(2-morpholinoethyl)-3-(3-(naphthalen-1-yloxy)propyl)-1H-indole-2-carboxylic Acid, S63845, omacataxine, seliciclib, UMI-77, AT101, sabutoclax or TW-37.

Method 90. The method according to any one of methods 59-78 further comprising the administration of a BCL-2 inhibitor.

Method 91. The method of method 90 wherein said BCL-2 inhibitor is venetoclax, navitoclax, ABT737, G3139 or S55746.

Method 92. The method according to any one of methods 59-91 wherein said treating is first line treatment in a non-adjuvant setting.

Method 93. A method of treating a subject for breast cancer comprising:
1) testing the subject for one or more ESR1 mutations; and
2) if the subject tests positive for one or more ESR1 mutations, treating the subject according to the method of any one of methods 1-35, 37-57, 59-92.

Method 94. The method of method 93 wherein said mutation results in reduced estradiol affinity for the mutated ESR1 compared to the non-mutated ESR1.

Method 95. The method according to method 93 or method 94 wherein said mutation signals ligand dependently or ligand independently through the ESR1 pathway.

Method 96. The method according to any one of methods 93-95 wherein said mutation results in a fusion protein containing at least 10 continuous amino acids from a sequence of a non-mutated ESR1 and at least 10 continuous amino acids from another human protein.

Method 97. The method according to any one of methods 93-95 wherein said mutation results in ESR1 missing 10 or more consecutive amino acids from its normal (non-mutated) ligand binding domain amino acid sequence.

Method 98. The method according to method 93 wherein said mutation is a fusion selected from the group consisting of ESR1-AKAP12, ESR1-CCDCl70, ESR1-YAP1, ESR1-POLH, ESR1-PCDH1IX, and combinations thereof.

Method 99. The method according to any one of methods 1-35, 37-57, 59-98 wherein said subject is first tested for baseline levels of mRNA or protein expression of ZBTB16 and then retesting for levels of mRNA or protein expression of ZBTB16 after a period of treatment and if the levels have increased over baseline, recommend that the subject continue therapy.

Method 100. The method according to method 99 wherein said period of treatment is at least 3 days of daily administration of an AR agonist.

Method 101. The method of method 100 wherein said period is at least one week of daily administration of an AR agonist.

Method 102. The method of any one of methods 99-101 wherein the ratio of post-treatment level to pre-treatment level is >3.

Method 103. The method of method 102 wherein the ratio is >10.

Method 104. The method of method 103 wherein the ratio is >50.

What is claimed is:

1. A method of treating AR+/ER+/HER2− breast cancer in a subject in need thereof, the method comprising administering to the subject a compound which is Compound III:

(Compound III)

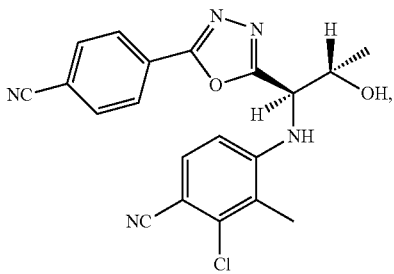

or a pharmaceutically acceptable salt or solvate thereof.

2. The method according to claim 1, wherein the compound is administered via an oral route.

3. The method according to claim 1, wherein:
(i) the subject is treated in an adjuvant setting;
(ii) the subject has had disease progression after treatment with one or more endocrinological agents; and/or
(iii) said subject has had disease progression after treatment with one or more agents selected from the group consisting of CDK4/6 inhibitors, mTOR inhibitors, BCL-2 inhibitors, PI3K inhibitors, and combinations thereof.

4. The method according to claim 1, wherein the breast cancer is resistant to at least one prior therapy.

5. The method according to claim 1, wherein the subject has progressed on prior endocrine therapy.

6. The method according to claim 1, wherein the subject is a candidate for first line treatment.

7. The method according to claim 1, wherein the compound is dosed between 10 and 500 mg, 10 mg and 250 mg, or 25 mg and 250 mg per day; optionally wherein the dose is once per day.

8. The method according to claim 1, wherein the subject expresses ESR1 comprising one or more mutations.

9. The method according to claim 8, wherein the one or more mutations is selected from the group consisting of ESR1-AKAP12, ESR1-CCDCl70, ESR1-YAP1, ESR1-POLH, ESR1-PCDH1 IX, and combinations thereof.

10. The method according to claim 1, wherein the subject expresses a PI3K mutation.

11. The method according to claim 10, wherein the PI3K mutation is PIK3CA.

12. The method according to claim 1, wherein the treatment further comprises the administration of a CDK4/6 inhibitor.

13. The method according to claim 12, wherein said CDK4/6 inhibitor is selected from the group consisting of palbociclib, ribociclib, trilaciclib, abemaciclib and AMG925.

14. The method according to claim 1, wherein said treatment further comprises the administration of a second therapeutic agent that targets the PI3K/AKT/mTOR pathway, for example:
(i) an mTOR inhibitor; optionally wherein said mTOR inhibitor is selected from the group consisting of sirolimus, temsirolimus, everolimus, ridafarolimus, and MLN0128; and/or
(ii) a PI3K inhibitor; optionally wherein said PI3K inhibitor is BEZ235, GDC-0980, GDC-0941, BYL719, MK2206, GDC-0068, GSK2110183, GSK2141795, AZD5363, AZD2014, MLN0128 or CC-223.

15. The method according to claim 1, wherein said treatment further comprises the administration of:
(i) a PARP inhibitor, for example talazoparib, veliparib, niraparib, beigene290, E7449, KX01, ABT767, CK102, JPI289, KX02, IMP4297, SC10914, NT125, PJ34, VPI289 or ANG-3186;
(ii) a MCL-1 inhibitor; optionally wherein said MCL-1 inhibitor is 7-(5-((4-(4-(N,N-Dimethylsulfamoyl)piperazin-1-yl)phenoxy)methyl)-1,3-dimethyl-1H-pyrazol-4-yl)-1-(2-morpholinoethyl)-3-(3-(naphthalen-1-yloxy)propyl)-1H-indole-2-carboxylic Acid, S63845, omacataxine, seliciclib, UMI-77, AT101, or sabutoclax; and/or
(iii) a BCL-2 inhibitor, for example venetoclax, navitoclax, ABT737, G3139 or S55746.

16. The method according to claim 1, wherein said treatment further comprises the administration of a therapeutic agent selected from the group consisting of rapamycin, everolimus, ridaforolimus, temsirolimus, MLN0128, CC115, CC223, OSI-027, AZD8055, AZD2014, GDC-0980, SAR245409, LY3023414, NVP-BEZ235, NVP-BGT226, SF1126 and PKI-587.

17. The method according to claim 1, wherein the treatment further comprises administration of a therapeutic agent selected from the group consisting of everolimus, BYL719, GDC-0068, palbociclib, AZD5363 and abemaciclib and combinations thereof.

18. The method according to claim 1, wherein the treatment further comprises the administration of everolimus.

19. The method according to claim 1, wherein the treatment further comprises the administration of BYL719.

20. The method according to claim 13, wherein the CDK4/6 inhibitor is palbociclib.

21. The method according to claim 13, wherein said CDK4/6 inhibitor is ribociclib.

22. The method according to claim 13, wherein said CDK4/6 inhibitor abemaciclib.

23. The method according to claim 1, wherein said subject is a woman.

24. The method according to claim 1, wherein said breast cancer is localized, advanced or metastatic.

25. The method according to claim 3, wherein said one or more endocrinological agents are selected from the group consisting of SERMs, SERDs, progestins, aromatase inhibitors, and combinations thereof.

26. The method according to claim 23, wherein said woman is a premenopausal woman or a post menopausal woman.

\* \* \* \* \*